United States Patent
Messing et al.

(10) Patent No.: US 11,242,536 B2
(45) Date of Patent: Feb. 8, 2022

(54) QUALITY PROTEIN MAIZE BASED ON INCREASED SULFUR REDUCTION IN LEAF CELLS

(71) Applicant: RUTGERS, THE STATE UNIVERSITY OF NEW JERSEY, New Brunswick, NJ (US)

(72) Inventors: Joachim Messing, Somerset, NJ (US); Jose Planta, East Lansing, MI (US)

(73) Assignee: RUTGERS, THE STATE UNIVERSITY OF NEW JERSEY, New Brunswick, NJ (US)

(*) Notice: Subject to any disclaimer, the term of this patent is extended or adjusted under 35 U.S.C. 154(b) by 0 days.

(21) Appl. No.: 16/650,290

(22) PCT Filed: Sep. 26, 2018

(86) PCT No.: PCT/US2018/052895
§ 371 (c)(1),
(2) Date: Mar. 24, 2020

(87) PCT Pub. No.: WO2019/067571
PCT Pub. Date: Apr. 4, 2019

(65) Prior Publication Data
US 2020/0231981 A1   Jul. 23, 2020

Related U.S. Application Data

(60) Provisional application No. 62/563,260, filed on Sep. 26, 2017.

(51) Int. Cl.
*C12N 15/82* (2006.01)
*C12N 9/02* (2006.01)

(52) U.S. Cl.
CPC ....... *C12N 15/8254* (2013.01); *C12N 9/0051* (2013.01); *C12N 15/8218* (2013.01); *C12N 2310/14* (2013.01)

(58) Field of Classification Search
None
See application file for complete search history.

(56) References Cited

U.S. PATENT DOCUMENTS

2011/0126319 A1* 5/2011 Catron ............... C12N 15/8247
800/281

OTHER PUBLICATIONS

Hall, White versus yellow maize as a pig and poultry food, Journal of the Department of Agriculture, Oct. 1923 (Year: 1923).*
Grunewald, Thirty years of transgenic plants, Nature, May 1, 2013 (Year: 2013).*
Martin, The role of 5' adenylylsulfate reductase in controlling sulfate reduction in plants, Photosynthesis Research, 2005 (Year: 2005).*
Tsakraklides, Sulfate reduction is increased in transgenic *Arabidopsis thaliana* expressing 5'-adenylylsulfate reductase from Pseudonmonas aeruginosa, The plant Journal, Dec. 20, 2002 (Year: 2002).*
Wu, Balancing of sulfur storage in maize seed, BMC Plant Biology, 2012 (Year: 2012).*
Wu, RNA Interference-Mediated Change in Protein Body Morphology and Seed Opacity through Loss of Different Zein Proteins, Plant Physiology, May 2010 (Year: 2010).*
Scott, Tryptophan and methionine levels in quality protein maize breeding germplasm, Agronomy Publications. 169, (2004) (Year: 2004).*
Guo, Nonredundant Function of Zeins and Their Correct Stoichiometric Ration Drive Protein Body Formation in Maize Endosperm, Plant Physiology, Jul. 2013 (Year: 2013).*
Doebley, The evolution of apical dominance in maize, Letters to Nature, Apr. 1997 (Year: 1997).*

* cited by examiner

*Primary Examiner* — Matthew R Keogh
*Assistant Examiner* — Brian James Sullivan
(74) *Attorney, Agent, or Firm* — Kathleen D. Rigaut; Howson & Howson LLP

(57) ABSTRACT

Compositions and methods to produce maize with improved nutritional content are disclosed.

Figure 1:
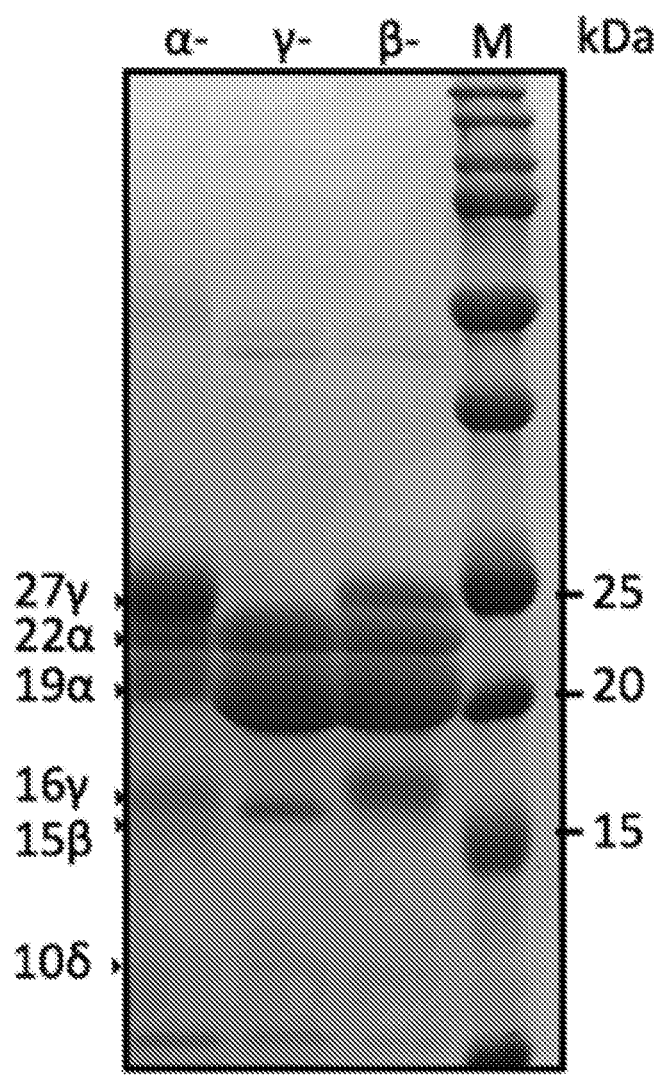

14 Claims, 10 Drawing Sheets
Specification includes a Sequence Listing.

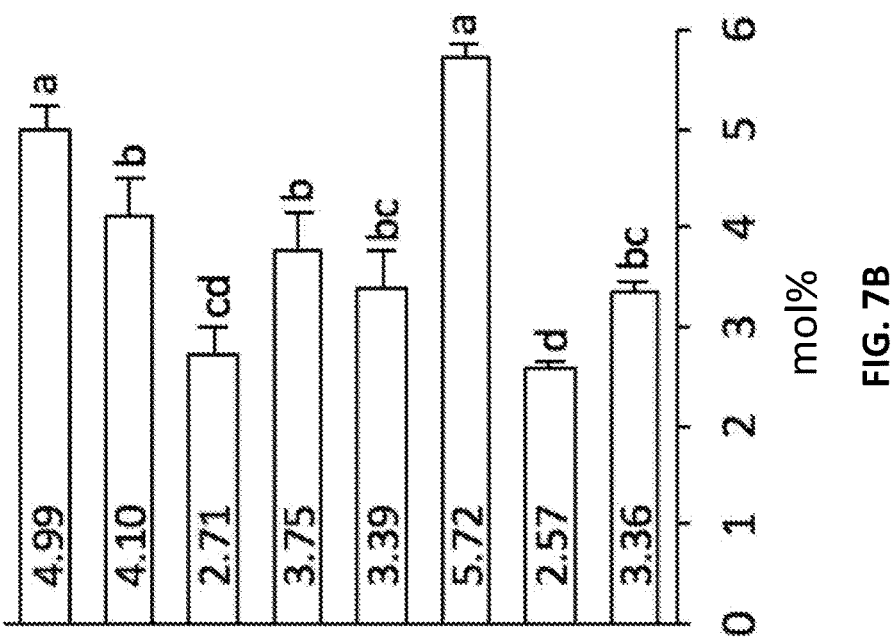
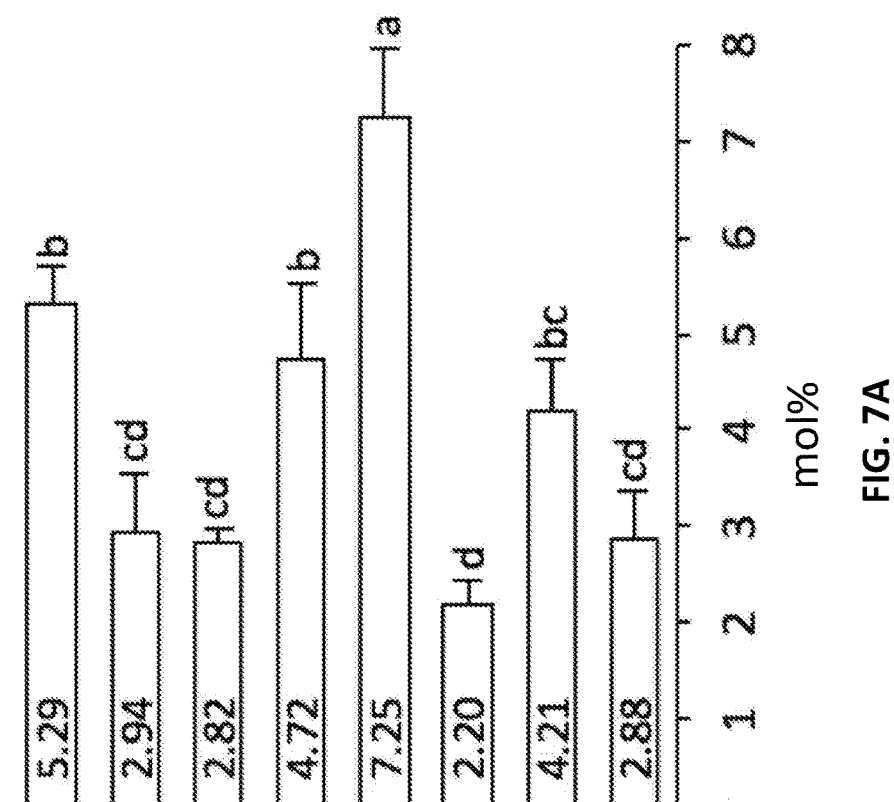
FIG. 7A
FIG. 7B

QUALITY PROTEIN MAIZE BASED ON INCREASED SULFUR REDUCTION IN LEAF CELLS

CROSS-REFERENCE TO RELATED APPLICATIONS

The present application is a § 371 of International Patent Application No. PCT/US2018/052895, filed Sep. 26, 2018 which claims the benefit of U.S. Provisional Application No. 62/563,260 filed Sep. 26, 2017. The entire disclosures of each of the foregoing applications are incorporated by reference herein as though set forth in full.

FIELD OF THE INVENTION

The present invention relates to field of plant genetic engineering. More specifically, the present invention provides compositions and methods useful for production of maize with improved protein quality and altered kernel phenotypes.

BACKGROUND OF THE INVENTION

Several publications and patent documents are cited throughout the specification in order to describe the state of the art to which this invention pertains. Each of these citations is incorporated herein by reference as though set forth in full.

In most developing countries, maize serves as the sole source of nutrition in human and animal diet, although its low protein content and quality necessitates its use in conjunction with other protein sources. Cereals like maize are limiting in the essential amino acids (EAAs) lysine (Lys), methionine (Met), and tryptophan, whereas legume crops like soybean are deficient in Met. Therefore, corn is usually supplemented with soybean and synthetic free methionine to provide a balanced amino acid diet for animal feed. A great deal of effort has been expended to genetically improve the amino acid balance of maize kernels, either through conventional selection breeding or the use of recombinant DNA technology.

Like other cereal grains, the maize kernel is made up of 6% pericarp, 12% germ, and 82% endosperm (Watson 1987). The bulk of the protein in a mature maize kernel resides in the endosperm, although the germ has a superior protein quality and higher protein content. Zeins in the endosperm make up the bulk of the protein in the mature maize kernel and possess an amino acid imbalance towards proline, glutamine, alanine, and leucine residues. The non-zein protein fraction in the endosperm (glutelins, globulins, and albumins) are relatively balanced in their amino acid composition (Prasanna et al. 2001). The abundance of zeins effectively dilutes the contribution of other endosperm proteins to the kernel Lys and tryptophan contents. It is not unexpected that alterations in the accumulation of zeins have led to the identification of mutants with altered nutritional quality. By increasing the accumulation of the β-, γ-, and δ-zeins relative to the more abundant α-zeins, we generated kernels with increased sulfur amino acid contents, effectively increasing its nutritional value (Planta et al.). On the other hand, reduction of α-zeins either through a transcriptional mutation (e.g., with the Opaque-2 or O2 protein) or a transgene that reduces its transcript accumulation through RNA interference (RNAi) resulted in more nutritionally-balanced endosperm proteins.

One of the thoroughly studied zein-reduction mutants, the recessive o2 mutant has about a 50% reduction in zein proteins (Tsai et al. 1978) and approximately double the amount of Lys compared with normal genotypes (Mertz et al. 1964). It primarily affects the synthesis of α-zeins, the 22-kDa α-zeins is barely detectable, whereas the 19-kDa α-zeins are greatly reduced (Jones et al. 1977). The o2 mutant, aside from a reduced Lys-poor zein content, has a compensating increase in the levels of Lys- and tryptophan-rich non-zein proteins. However, the soft and starchy endosperm producing the opaque phenotype observed in o2 kernels makes it susceptible to fungi and insect infestation, both in storage and in the field (NRC 1988). Identification of o2 modifiers (mot) (suppressors) that can restore the normal kernel phenotype while maintaining the increased EAA content of o2 permitted the development of a new type of maize germplasm, known as quality protein maize (QPM) (Prasanna et al. 2001).

On the other hand, transforming maize with a transgene targeting the α-zeins through RNAi resulted in maize kernels with enhanced levels of Lys and tryptophan (Segal et al. 2003; Huang et al. 2004; Huang et al. 2006). The observed increase in Lys and tryptophan in the α-zein-reduced kernels was also due to the replacement of the Lys-poor zeins with the Lys-containing non-zein proteins (Huang et al. 2006). Doubling the Lys levels without changing the protein content in corn could add up to $480 million in annual gross value to US corn in the global feed market (Johnson et al. 2000).

Among the opaque mutants that affect the accumulation of the zeins, only two have been reported that alter the synthesis of the γ-zeins. The maize Mucronate mutation is a deletion in the 16-kDa γ-zein that produces an abnormal 16-kDa γ-zein, whereas opaque-15 reduces the 27-kDa γ-zein synthesis and appears to be a mutation of an o2 modifier gene (Dannenhoffer et al. 1995; Kim et al. 2006). Near-isogenic lines of several high-Lys opaque mutants in the W64A genetic background showed that o2 has the highest kernel Lys content among the opaque mutants (Hunter et al. 2002). Efforts to improve the protein quality of maize seeds have focused on o2 seeds as other opaque mutants offer no additional advantage over o2 in terms of Lys content and nutritional quality. Clearly a need exists in the art for new approaches to producing maize plants with improved nutritional content.

SUMMARY OF THE INVENTION

In accordance with the present invention, a method for obtaining maize with kernels that have altered essential amino acid content is provided. An exemplary method entails crossing a maize plant that has a transgene for leaf-specific expression of 3'-phosphoadenosine-5'-phosphosulfate reductase (PAPR) enzyme with another maize plant that has a RNAi transgene that downmodulates expression of one or more of α-zein, β-zein, and γ-zein. In certain embodiments, at least one of the maize plants is High-Met. In accordance with another aspect, the PAPR enzyme is operably linked to a PepC promoter. In a further aspect, the present invention provides a method where the RNAi transgene has at least one selectable marker or reporter gene, thereby facilitating identification of progeny having the RNAi transgene. In certain embodiments, the maize plant expresses RNAi transgenes targeting α-zein and γ-zein or α-zein and β-zein such as those described in U.S. Pat. No. 9,603,317, which is incorporated herein by reference as though set forth in full.

In accordance with another aspect, the present invention provides a maize plant with kernels that have altered essential amino acid content. This method comprises crossing a maize plant having a transgene for leaf-specific expression of 3'-phosphoadenosine-5'-phosphosulfate reductase (PAPR) enzyme with another maize plant that has a RNAi transgene that downmodulates expression of one or more of α-zein, β-zein, and γ-zein. In certain embodiments, the maize plant expresses an RNAi transgene targeting γ-zein and has kernels with a vitreous phenotype and increased Met and Lys content. In a further aspect, the maize plant expresses RNAi transgenes targeting α-zein and γ-zein and has kernels with an opaque phenotype and increased Met and Lys content. In yet a further aspect, the maize plant has elevated levels of GLB1 and elevated kernel Lys content. The present invention also provides for compositions with kernels or ground kernel material obtained from maize plants that have altered essential amino acid content.

In accordance with another aspect, the present invention provides a method for obtaining a maize plant with kernels that have altered essential amino acid content by crossing a maize plant that has a transgene for leaf-specific expression of 3'-phosphoadenosine-5'-phosphosulfate reductase (PAPR) enzyme with another maize plant that has a RNAi transgene that downmodulates expression of one or more of α-zein, β-zein, and γ-zein and breeding the transgenic plant obtained from the cross to yield a progeny plant that also has a PAPR transgene and a RNAi transgene. The present invention also provides for the seed or progeny resulting from the crosses described herein.

BRIEF DESCRIPTIONS OF THE DRAWINGS

FIG. 1. Differential accumulation of the zeins in 15% SDS-PAGE gel in different zein reduction lines. α– has an RNAi that targets the 19- and 22-kDa α-zeins, γRNAi (γ-) targets both the 16- and 27-673 kDa γ-zeins while βRNAi (β-) promotes knockdown of expression of the 15-kDa β-zein. γRNAi and βRNAi are in a hybrid Hi II A×B and A654 backgrounds while αRNAi is in a Hi II A×B background.

Figure 2A:
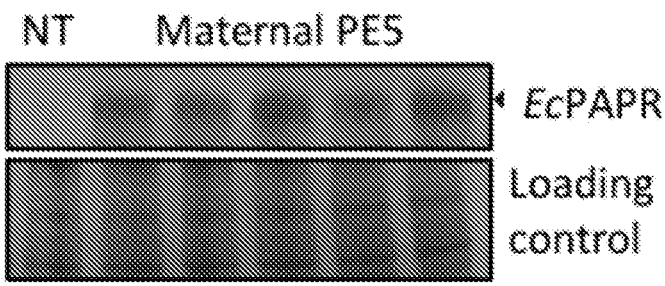
Figure 2B:
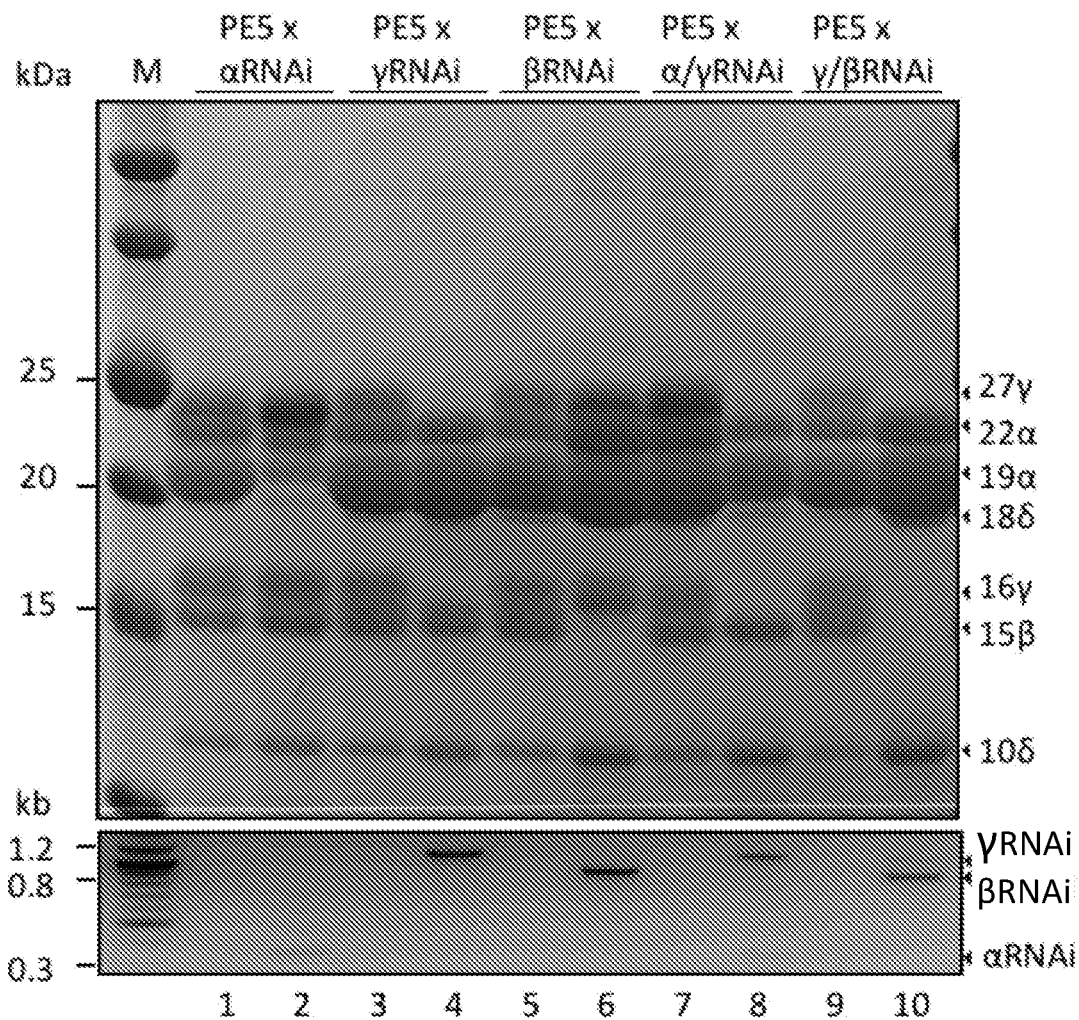

FIGS. 2A-2B. Zein profiles of kernels from crosses of PE5 with RNAi lines targeting the α–, γ–, α–/γ–, or γ–/β-zeins. (FIG. 2A) Western blotting for detection of exogenous expression of the bacterial EcPAPR in leaf tissues of PE5 plants, which were used as the maternal parents for crossing with the zein reduction lines. (FIG. 2B) SDS-PAGE zein profiles (upper panel) of segregating populations of kernels from PE5×zein RNAi crosses. Kernels non-segregating (odd-numbered lanes) and segregating (even-numbered lanes) for the RNAi transgenes were pooled and used for analysis. The RNAi transgenes in these segregating populations were detected by AGE (lower panel).

FIGS. 3A-3I. Endosperm phenotypes of transgenic zein reduction kernels (upper panels) sliced in half to reveal the degree of vitreous endosperm (lower panels). (FIGS. 3A, 3D, 3F, and 3G) Zein RNAi and (FIGS. 3B, 3C, 3E, 3H, 3I) PE5; zein RNAi lines. γRNAi and βRNAi are in a hybrid Hi II A×B and A654 backgrounds, αRNAi is in a Hi II A×B background, and PE5 was backcrossed twice to B101 prior to being crossed with the RNAi lines. PE5; α– is in a Hi II AB× and B101 backgrounds while remaining PE5; zein RNAi lines are in a hybrid background of Hi II A×B, B101, and A654. Restoration of the semi-vitreous or vitreous phenotypes by the high-Met maternal background of PE5 is observed in kernels with reduction of γ-zeins and γ–/β-zeins, respectively.

Figure 4:
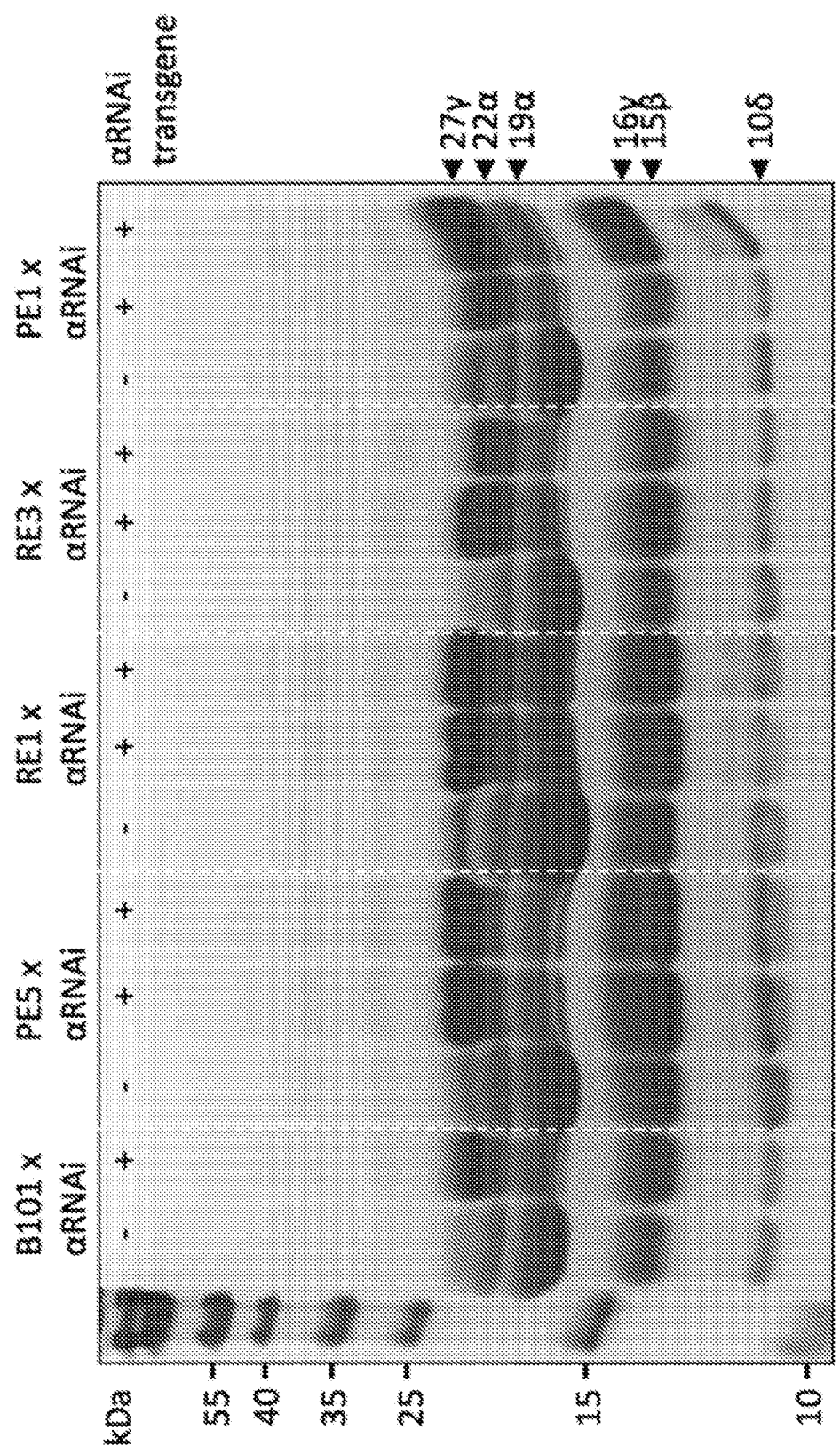

FIG. 4. Zein profiles of segregating populations of kernels from crosses of α-zein RNAi with different EcPAPR transgenic events. Kernels segregating (+) and non-segregating (–) for the αRNAi transgene were pooled and separated in a 15% SDS-PAGE gel. The presence of the αRNAi transgene in the kernel increased accumulation of the 27-kDa γ-zein.

Figure 5C:
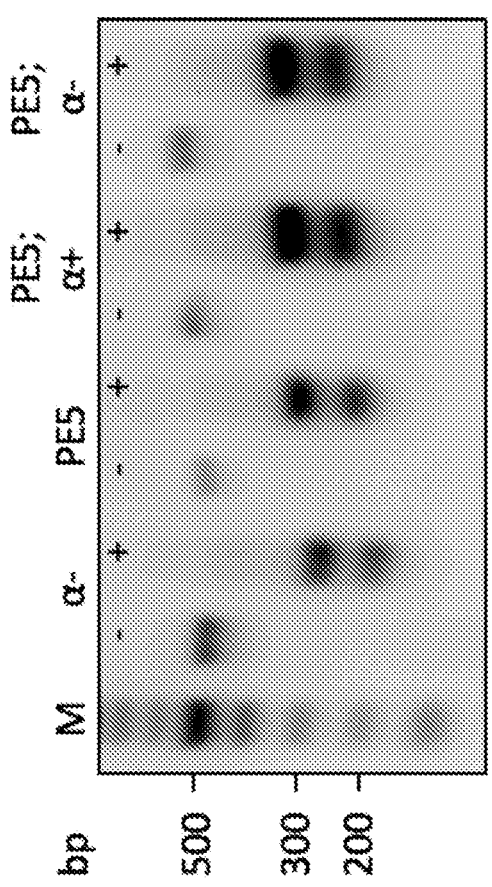
Figure 5A:
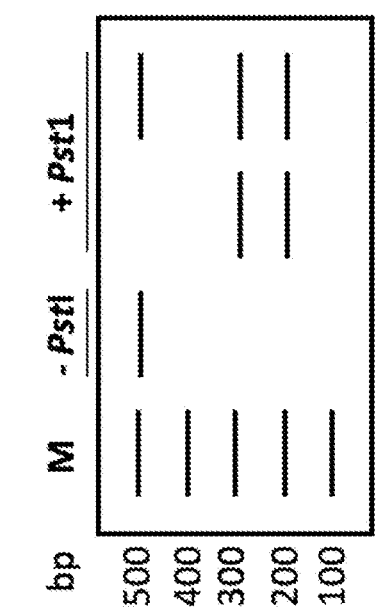
Figure 5B:
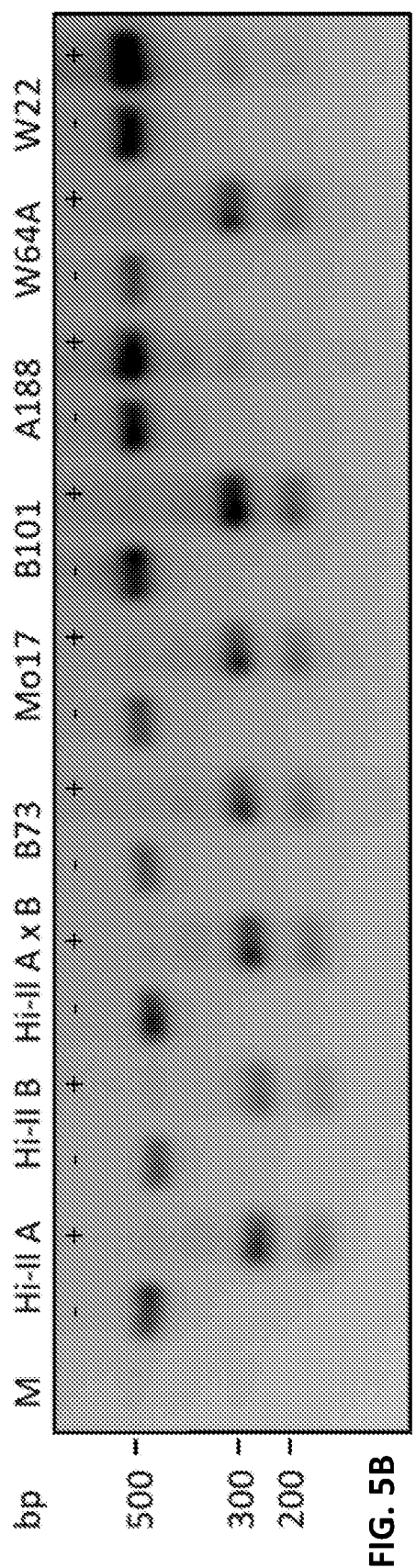

FIGS. 5A-5C. Cleaved amplified polymorphic sequence (CAPS) assay to determine allelic variation of the 27-kDa γ-zein gene in different maize genotypes. (FIG. 5A) Diagram showing amplified DNA fragments of the 27-kDa γ-zein gene displaying restriction fragment length polymorphisms when digested with PstI, depending on the allelic variation of the gene. The single-copy Rb allele resulted from recombination of the tandemly-duplicated A and B alleles of the 27-kDa γ-zein gene (Das et al. 1991). (FIG. 5B) Different maize inbred lines and the hybrid Hi-II A×B were tested with the CAPS assay to determine the variation in their 27-kDa γ-zein gene. The inbred lines A188 and W22 have tandemly duplicated copy while the remaining maize genotypes tested have the single-copy allele of the gene. (FIG. 5C) Maize genotypes corresponding to the parental PE5 and α-zein RNAi lines and the resulting progeny kernels from the cross have the same allele of the 27-kDa γ-zein gene. PE5; α+ and PE5; α– refer to kernels resulting from the cross of the maternal PE5 with the α-zein RNAi and that are non-segregating and segregating for the α-zein RNAi transgene, respectively.

Figures 6A, 6B:
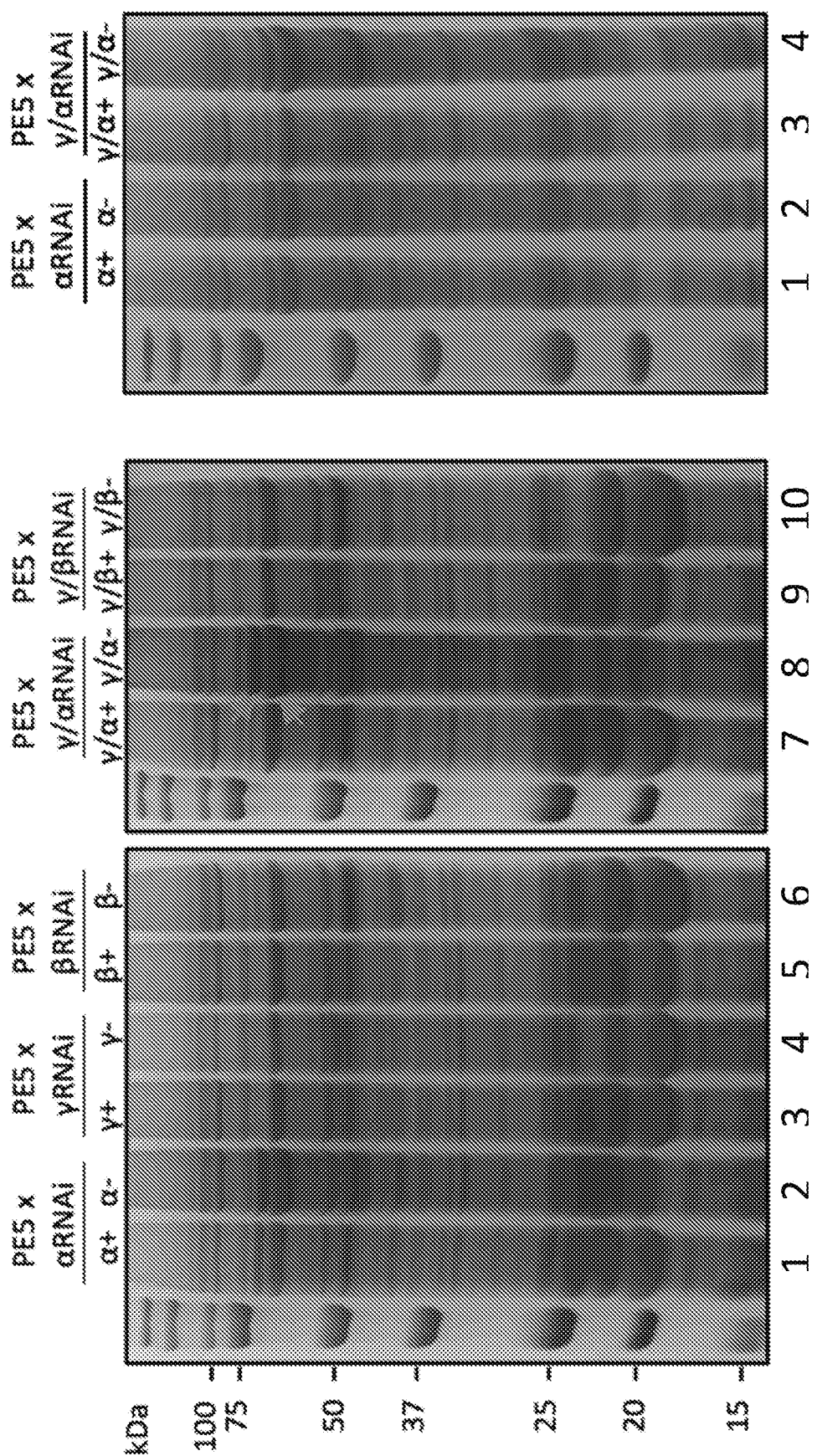

FIGS. 6A-6B. Total seed proteins (FIG. 6A) and non-zein proteins (FIG. 6B) from transgenic progeny kernels from crosses of PE5 with RNAi lines targeting the α–, β–, γ–, β–/γ–, or α–/γ-zeins separated in a 12% SDS-polyacrylamide gel. Kernels non-segregating (odd-numbered lanes) and segregating (even numbered lanes) for the RNAi transgenes were pooled and used for analysis. Red arrows indicate proteins in the ~65-70 kDa range that have increased accumulation in kernels segregating for the α– and α–/γ-zein RNAi transgenes. The identities of these protein bands were determined by MS analysis.

FIGS. 7A-7B. Total seed Lys (FIG. A) and Met (FIG. 7B) content. Values are means from three independent measurements of pooled samples and error bars indicate standard deviation. Statistical analysis was performed by using the one-way analysis of variance with post-hoc Tukey HSD test; significant differences between samples are indicated by different letters.

Figure 8:
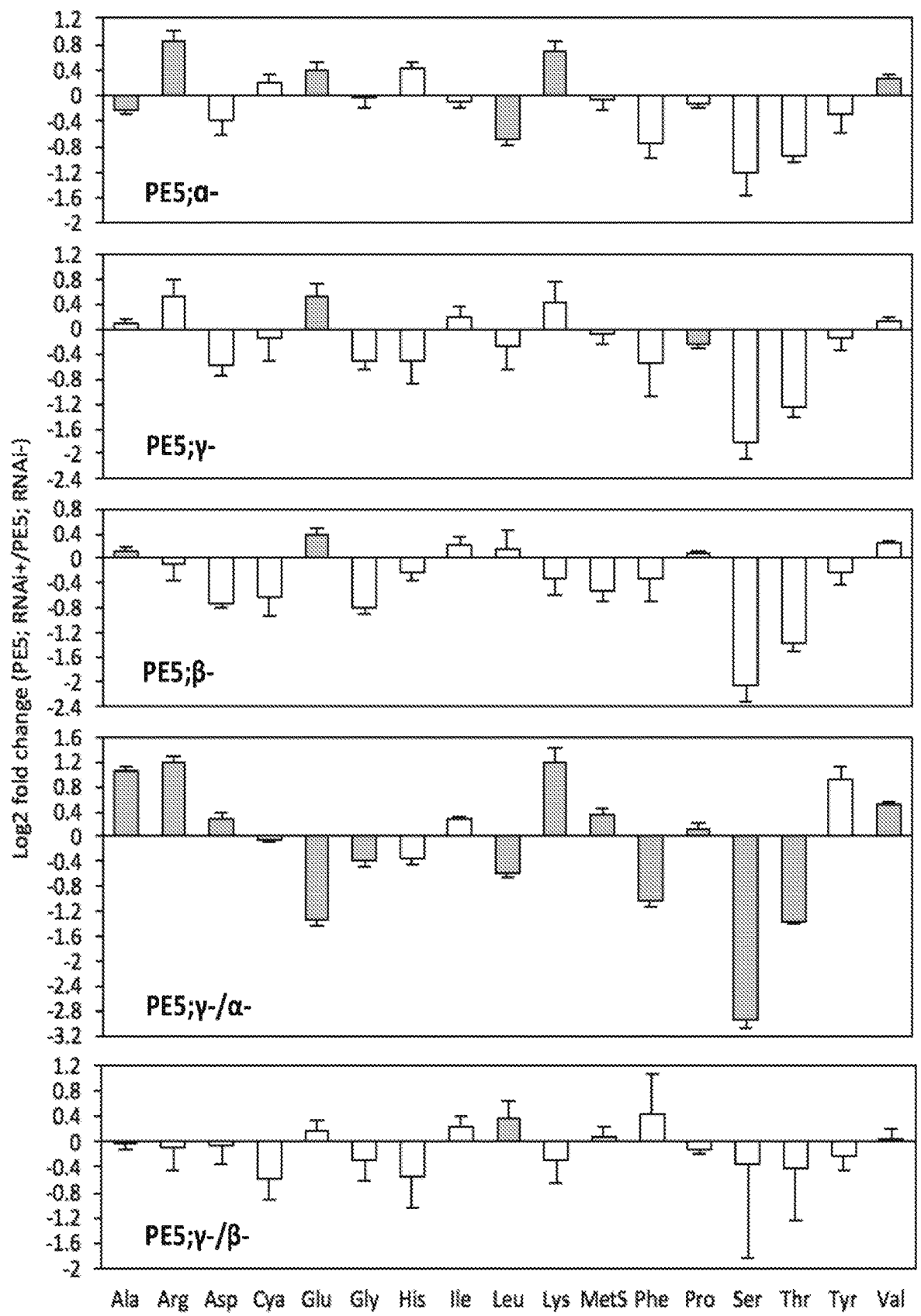

FIG. 8. Amino acid composition analysis of segregating kernels from a cross of the maternal PE5 with the zein RNAi lines. Kernels from an ear resulting from the cross and segregating or non-segregating for the RNAi transgene(s) were pooled and used for analysis. Shown are changes in the amino acid composition of PE5;α–, PE5;γ–, PE5;β–, PE5; γ–/α–, and PE5;γ–/β– relative to the corresponding controls of PE5; RNAi- kernels. Cya and MetS refer to cysteic acid and Met sulfone, respectively, the acid stable forms of cysteine and Met produced after performic acid treatment of the sample. Values are means from three independent measurements of pooled samples and error bars indicate standard deviation. Boxes in green denote that values for the PE5; RNAi+kernels are statistically different from the corresponding control at p<0.01.

Figure 9A:
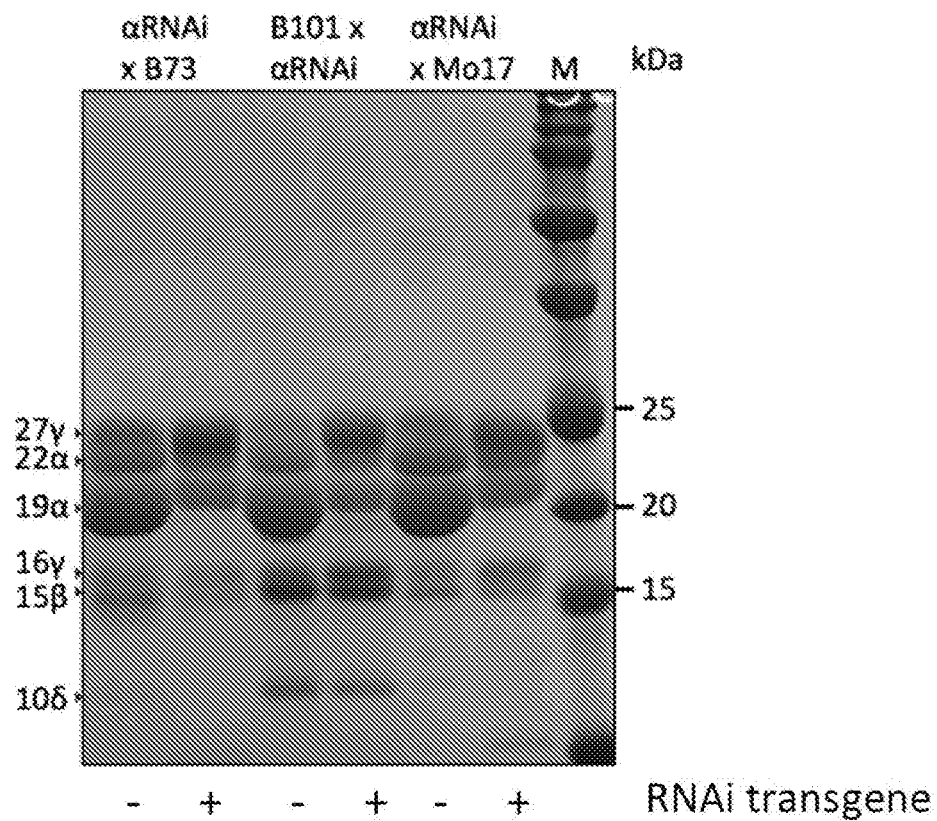
Figure 9B:
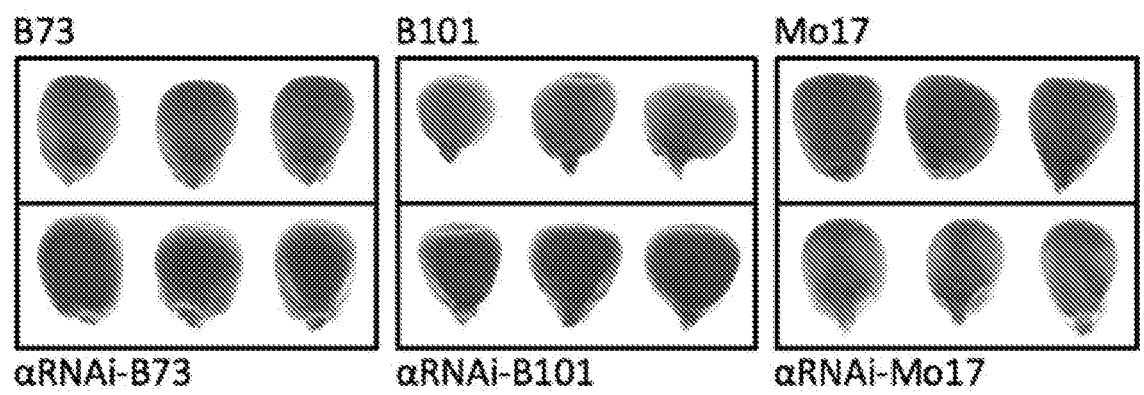

FIGS. 9A-9B. Protein accumulation profiles and phenotypes of hybrid kernels. (FIG. 9A) Zein profiles of segregating populations of kernels from crosses of the α-zein RNAi line with the inbred lines B73, B101, and Mo17. The presence of the RNAi transgene in the kernel increased accumulation of the 27-kDa γ-zein. (FIG. 9B) Endosperm phenotypes of kernels segregating for the α-zein RNAi transgene (lower panels), as viewed over a light box, resulting from a cross of the α-zein RNAi with the inbreds B73, B101, and Mo17. Kernels that do not segregate for the RNAi transgene from these crosses are on the upper panels. Restoration of the vitreous phenotype is observed in the hybrid αRNAi-Mo17 kernels.

Figure 10:
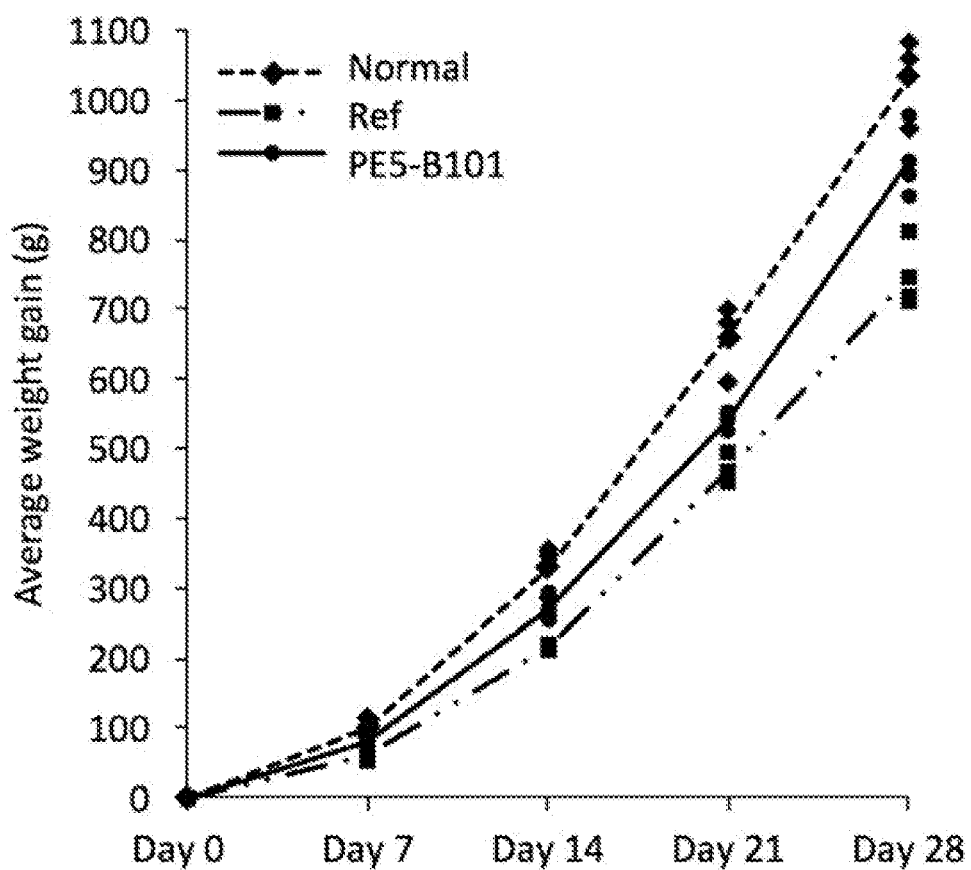

FIG. 10. Feeding trial with the transgenic high-Met PE5 maize. A 4-wk feeding trial with 5-d-old chicks was carried out with three types of diets consisting of yellow dent corn supplemented with synthetic methionine (normal group), PE5-B101 without synthetic methionine, and the null transgenic segregant from PE5-B101 without methionine supplementation (reference group). Shown in the graph is the average weight gain, denoted by the lines, during the course of the experiment, and the table shows the weight gain and feed intake per chick at the conclusion of the feeding trial. Weight gain is calculated as the difference between the finishing and starting weights, and the feed conversion ratio is the amount of food consumed per gained weight. Statistical analysis was performed with two-way ANOVA at $P<0.05$, and significant differences between samples are indicated by different letters. Data shown are means±SD of three replicates with five animals per replicate.

DETAILED DESCRIPTION OF THE INVENTION

Low levels of the essential amino acids Lys and Met in a maize-based diet represent a major cost in the world food supply. Lys deficiency is due to the abundance of Lys-poor α-zeins in maize endosperm. However, a maize variant was discovered with a mutation rendering the transcription factor inactive that controlled the expression of α-zeins, known as o2 due to the opaque appearance of the maize kernel. Although o2 maize has sufficient levels of Lys, its soft kernel renders it unfit for storage and transportation. Breeders overcame this problem by selecting quantitative trait loci (QTLs) restoring kernel hardness in the presence of o2, a variety called Quality Protein Maize (QPM). Although some QTLs act by enhancing the expression of γ-zeins, we surprisingly achieved rebalancing of the Lys content and a vitreous kernel phenotype with low levels of γ-zeins and without the o2 mutation by crossing two previously generated transgenic events. Levels of γ-zeins were reduced with RNA interference (RNAi). The other transgenic event, named PE5, expresses the *E. coli* enzyme 3' phosphoadenosine-5'-phosphosulfate reductase, an enzyme involved in reductive sulfate assimilation in the leaf. Kernels of the genotypes PE5; α-/γ- and PE5;γ- have Lys and Met contents higher than the mutant o2 in the W64A maize genetic background (W64Ao2). Although the opaque PE5;α-/γ- kernels have higher Met and Lys contents than the vitreous PE5;γ- kernels, a vitreous phenotype would be worth the compromise for commercial applications. PE5 with a single dominant RNAi-inducing transgene of γ-zein is a superior QPM variety because of higher Lys and elevated Met levels. Moreover, due to the increased sulfur reduction in leaf cells, even the level of Met is elevated in the seed. Such a combination of genes produces hybrid seeds superior to classical QPMs that require neither a costly feed mix nor synthetic Met supplementation, thereby revolutionizing food production.

Sulfur assimilation appears to limit the pool of methionine and cysteine available for incorporation into zeins, the major seed storage proteins in maize. The transgenic kernels described herein have higher expression of the methionine-rich 10-kDa δ-zein and total protein sulfur without reduction of other zeins. This overall increase in the expression of the S-rich zeins describes a facet of regulation of these proteins under enhanced sulfur assimilation. Transgenic line PE5 accumulates 57.6% more kernel methionine than the high-methionine inbred line B101. In feeding trials with chicks, PE5 maize promotes significant weight gain compared with non-transgenic kernels. Therefore, increased source strength can improve the nutritional value of maize without apparent yield loss and should significantly reduce the cost of feed supplementation.

Poultry feed is usually prepared as a corn-soybean mixture. Because the only essential sulfur amino acid missing in this mixture is methionine, it is chemically synthesized and added separately, increasing the cost of major food supply. It appears to be difficult to circumvent the regulatory aspects of sulfur metabolism, which is controlled at many levels, without damage to plant growth. By using tissue-specific promoters to express a bacterial enzyme that increases the efficiency of assimilative sulfate reduction, seed methionine accumulation can be increased without the concomitant accumulation of toxic metabolites. We show that even in maize inbred lines with repressed seed methionine levels, sink strength can be increased to the benefit of feed consumption efficiency in chicks.

The following definitions are provided to facilitate an understanding of the present invention.

For purposes of the present invention, "a" or "an" entity refers to one or more of that entity; for example, "a RNAi" refers to one or more RNAi or at least one RNAi. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated, or biologically pure molecule is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the functional and novel characteristics of the sequence.

"Target nucleic acid" as used herein refers to a previously defined region of a nucleic acid present in a complex nucleic acid mixture wherein the defined wild-type region contains at least one known nucleotide variation which may or may not be associated with disease. The nucleic acid molecule may be isolated from a natural source by cDNA cloning or subtractive hybridization or synthesized manually. The nucleic acid molecule may be synthesized manually by the triester synthetic method or by using an automated DNA synthesizer.

As used herein, "genetically modified" or "genetically altered" means the modified expression of a seed protein resulting from one or more genetic modifications; the modifications including but not limited to: recombinant gene technologies, induced mutations, and breeding stably genetically modified plants to produce progeny comprising the altered gene product. Transgenic plants producing seeds and grain with altered zein protein content are also provided.

The terms "decrease", "decreased", and "decreasing" or "increase", "increased," and "increasing" are intended to refer to a change in measurement of a parameter by at least 10%, 20%, 30%, 40%, 50%, 60%, 70%, 80%, 90%, 100%, 200% or more when compared to the measurement of that parameter in a suitable control.

The compositions and methods of the invention are useful for modulating the levels of at least one seed protein in seeds. By "modulate" is defined herein as an increase or decrease in the level of a seed protein within seed of a genetically altered plant relative to the level of that protein in seed from the corresponding wild-type plant (i.e., a plant not genetically altered in accordance with the methods of the present invention).

The terms "inhibit," "inhibition," "inhibiting", "reduced", "reduction" and the like as used herein refer to any decrease in the expression or function of a target gene product, including any relative decrement in expression or function up to and including complete abrogation of expression or function of the target gene product.

The term "expression" as used herein in the context of a gene product refers to the biosynthesis of that gene product, including the transcription and/or translation of the gene product. Inhibition of expression or function of a target gene product (i.e., a gene product of interest) can be in the context of a comparison between any two plants, for example, expression or function of a target gene product in a genetically altered plant versus the expression or function of that target gene product in a corresponding wild-type plant. Alternatively, inhibition of expression or function of the target gene product can be in the context of a comparison between plant cells, organelles, organs, tissues, or plant parts within the same plant or between plants, and includes comparisons between developmental or temporal stages within the same plant or between plants. Any method or composition that down-regulates expression of a target gene product, either at the level of transcription or translation, or down-regulates functional activity of the target gene product can be used to achieve inhibition of expression or function of the target gene product.

The term "inhibitory sequence" encompasses any polynucleotide or polypeptide sequence that is capable of inhibiting the expression of a target gene product, for example, at the level of transcription or translation, or which is capable of inhibiting the function of a target gene product.

When the phrase "capable of inhibiting" is used in the context of a polynucleotide inhibitory sequence, it is intended to mean that the inhibitory sequence itself exerts the inhibitory effect; or, where the inhibitory sequence encodes an inhibitory nucleotide molecule (for example, hairpin RNA, miRNA, or double-stranded RNA polynucleotides), or encodes an inhibitory polypeptide (i.e., a polypeptide that inhibits expression or function of the target gene product), following its transcription (for example, in the case of an inhibitory sequence encoding a hairpin RNA, miRNA, or double-stranded RNA polynucleotide) or its transcription and translation (in the case of an inhibitory sequence encoding an inhibitory polypeptide), the transcribed or translated product, respectively, exerts the inhibitory effect on the target gene product (i.e., inhibits expression or function of the target gene product).

The term "RNA interference" or "RNAi" refers generally to a process or system in which a RNA molecule changes the expression of a nucleic acid sequence with which RNA molecule shares substantial or total homology. The term "RNAi agent" refers to an RNA sequence that elicits RNAi.

In many instances the nucleotide sequences for use in the methods of the present invention, are provided in transcriptional units with for transcription in the plant of interest. A transcriptional unit is comprised generally of a promoter and a nucleotide sequence operably linked in the 3' direction of the promoter, optionally with a terminator.

"Operably linked" refers to the functional linkage between a promoter and a second sequence, wherein the promoter sequence initiates and mediates transcription of the DNA sequence corresponding to the second sequence. The expression cassette will include 5' and 3' regulatory sequences operably linked to at least one of the sequences of the invention.

Generally, in the context of an over expression cassette, operably linked means that the nucleotide sequences being linked are contiguous and, where necessary to join two or more protein coding regions, contiguous and in the same reading frame. In the case where an expression cassette contains two or more protein coding regions joined in a contiguous manner in the same reading frame, the encoded polypeptide is herein defined as a "heterologous polypeptide" or a "chimeric polypeptide" or a "fusion polypeptide". The cassette may additionally contain at least one additional coding sequence to be co-transformed into the organism. Alternatively, the additional coding sequence(s) can be provided on multiple expression cassettes.

The methods of transgenic expression can be used to modulate the level of at least one seed protein in grain or corn. The methods of transgenic expression comprise transforming a plant cell with at least one expression cassette comprising a promoter that drives expression in the plant operably linked to at least one nucleotide sequence. Methods for expressing transgenic genes in plants are well known in the art.

DNA constructs or vectors of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Transformed plant cells that are derived by any of the above transformation techniques can be cultured to regenerate a whole plant that possesses the transformed genotype and thus the desired phenotype. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al., Ann. Rev. of Plant Phys. 38:467-486 (1987).

One of skill will recognize that after the expression cassette or vector is stably incorporated in transgenic plants and confirmed to be operable, it can be introduced into other plants by sexual crossing. Any of a number of standard breeding techniques can be used, depending upon the species to be crossed.

Plant transformants containing a desired genetic modification as a result of any of the above described methods resulting in decreased or increased expression of the seed protein of the invention can be selected by various methods known in the art. These methods include, but are not limited to, methods such as SDS-PAGE analysis, immunoblotting using antibodies which bind to the seed protein of interest, single nucleotide polymorphism (SNP) analysis, or assaying for the products of a reporter or marker gene, and the like.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. GFP is exemplified herein. The nucleic acid may be either RNA or DNA, linear or circular, single or double stranded, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence which hybridizes to any IM sensitivity marker gene or nucleic acid, but does not hybridize to other nucleotides. Also polynucleotide which "specifically hybridizes" may hybridize only to a IM sensitivity marker shown in the Tables contained herein. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., *Molecular Cloning*, Cold Spring Harbor Laboratory (1989)):

$$T_m = 81.5° C. + 16.6 \text{ Log } [Na+] + 0.41(\% \text{ G+C}) - 0.63$$
$$(\% \text{ formamide}) - 600/\#bp \text{ in duplex}$$

As an illustration of the above formula, using $[Na+] = [0.368]$ and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

The term "oligonucleotide," as used herein is defined as a nucleic acid molecule comprised of two or more ribo- or deoxyribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides are at least about 10 nucleotides in length, more preferably at least 15 nucleotides in length, more preferably at least about 20 nucleotides in length.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25, 30, 50, 75 or more nucleotides nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complimentary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

The introduced nucleic acid may or may not be integrated (covalently linked) into nucleic acid of the recipient cell or organism. In plant cells, for example, the introduced nucleic acid may be maintained as an episomal element or independent replicon, such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The terms "recombinant organism," or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. Therefore, the phrase "a recombinant organism" encompasses a recombinant cell, as well as a eukaryotic and a prokaryotic organism.

Promoters useful in some embodiments of the present invention may be tissue-specific or cell-specific. The term "tissue-specific" as it applies to a promoter refers to a promoter that is capable of directing selective expression of a nucleotide sequence of interest to a specific type of tissue in the relative absence of expression of the same nucleotide sequence of interest in a different type of tissue (e.g., flower vs. root vs. leaf).

The following example is provided to illustrate certain embodiments of the invention. It is not intended to limit the invention in any way.

EXAMPLE

Using two disparate transgenic mechanisms to deregulate amino acid biosynthesis and zein reduction, we generated plants that are enriched in both Lys and Met.

Materials and Methods

Genetic Stocks

The α, γ, and βRNAi transgenic plants were from our laboratory stocks and have been described elsewhere (Wu and Messing 2010; Wu and Messing 2011; Wu et al. 2012; U.S. Pat. No. 9,603,317). Both the γRNAi and βRNAi are homozygous for A654-Dzs10, a nonfunctional allele of the 10-kDa δ-zein gene from the inbred A654. The βRNAi plant used for crosses is homozygous for the RNAi transgene as all kernel progenies tested positive for βRNAi genotyping, whereas the γRNAi is hemizygous, as about half of the tested kernel progenies from crosses with γRNAi had the RNAi transgene. αRNAi, on the other hand, is in an A×B hybrid background and is hemizygous for the RNAi transgene. The transgenic event PE5 was backcrossed twice to the high-Met inbred line B101 prior to being crossed with the RNAi lines. It ectopically expresses the *Escherichia coli* enzyme 3'-phosphoadenosine-5'-phosphosulfate reductase, designated as EcPAPR (Martin et al. 2005), driven by the PepC promoter (Sattatzadeh et al. 2010). EcPAPR is involved in assimilatory sulfate reduction and maize plants expressing this enzyme shows increased kernel Met content when used as the maternal parent (Tarczynski et al. 2003; Martin et al. 2005). Also see U.S. Pat. No. 6,576,819, incorporated herein by reference. Crosses between the maternal PE5 and the paternal RNAi lines were performed. PE5;γ– plants generated were crossed with αRNAi. We also crossed γ/βRNAi, βRNAi, and αRNAi with PE5. All in all, these crosses gave five distinct ears that were used for analysis: (1) PE5;α–, (2) PE5;β–, (3) PE5;γ–, (4) PE5;γ–/β–, and (5) PE5;γ–/α–.

Genotyping

Genomic DNA was isolated from maize leaves at the 3- to 4-leaf stage using a modified CTAB extraction method (Sawa et al. 1997). For extraction of genomic DNA from mature maize kernels, a portion of the kernel that is mostly endosperm with no embryo tissues were ground to a fine powder and subjected to DNA extraction with the Nucleospin Plant II kit (Takara Bio USA). Transgenic plants were screened for the presence of both RNAi and EcPAPR transgenes using the primer pairs 5'-ACAACCACTACCT-GAGCAC-3' (SEQ ID NO: 1)/5'-ATTAAGCTTTGCAGGT-CACTGGATTTTGG-3' (SEQ ID NO: 2) (Wu and Messing 2010) and 5'-CTCCCCATCCCTATTTGAACCC-3' (SEQ ID NO: 3)/5'-GGTAGGTTTCCGGGAACAAGTA-3' (SEQ ID NO: 4), respectively. PCR amplification for the RNAi transgenes produced amplicons of the sizes 365, 913, and 1,096 bp corresponding to α–, β–, and γRNAi lines, respectively, whereas screening for PE5 yields a 696-bp product. Kernels from an ear segregating and non-segregating for the RNAi transgenes were pooled separately and used for DNA extraction and genotyping. The 27-kDa γ-zein gene displays allelic variation and differential expression and exists as a tandemly-duplicated or single-copy gene depending on the genetic background (Das and Messing 1987). To determine possible allelic variation between different maize genotypes, amplified DNA fragments of the 27-kDa γ-zein gene were digested with PstI to display restriction fragment length polymorphisms (Konieczny and Ausubel 1993). Primers 5'-CCACCTCCACGCATACAAG-3'; (SEQ ID NO: 5) and 5'-ATGGACTGGAGGACCAAGC-3' (SEQ ID NO: 6) were used to amplify a 487-bp fragment of the 27-kDa γ-zein gene spanning positions 50 to 546 of the coding region (Das et al. 1991). Digestion with PstI would produce three DNA fragments (487, 292, and 195 bp), when the gene exists as a tandem copy or only two fragments for a single-copy gene (292 and 195 bp).

Analysis of Transgenic Plants

Protein Extraction, SDS-PAGE Analysis, and Western Blotting

Total protein from pooled endosperm samples of mature maize kernels were extracted with an alkaline sodium borate extraction buffer (Wallace et al. 1990), whereas the alcohol-soluble zeins from the endosperm of mature maize kernels were fractionated and separated in SDS-PAGE as previously described (Wu and Messing 2010).

Mature maize kernels were imbibed in water for two days to facilitate easier separation of the embryo from the endosperm. Proteins were isolated from embryos macerated in an SDS sample buffer [10% (v/v) glycerol, 2.3% (w/v) SDS, 5% (v/v) β-mercaptoethanol, 62.5 mM Tris-Cl, pH 6.8] at a ratio of 50 mg tissue/ml of buffer and the extracts processed as described previously (Belanger and Kriz 1989; Puckett and Kriz 1991).

Total protein from three mature maize leaf discs was extracted following the procedure of Conlon and Salter (2007). Ten microgram of total protein was separated in a 12% Tris-glycine SDS-PAGE gel and immunoblotted with an antibody against EcPAPR kindly provided by Dr. Jens Schwen (Krone et al. 1991). For immuno-detection, the secondary antibody is a goat anti-rabbit peroxidase conjugate (Sigma-Aldrich) and was used at a 1:60,000 dilution while the primary anti-EcPAPR antibody in a TBST buffer with 0.5% BSA was used at a 1:4,000 dilution.

Protein Identification

Protein bands that have differential accumulation in kernels segregating for the α-zein RNAi transgene were excised out of the SDS-polyacrylamide gel and analyzed by trypsin-nano-LC-MS using Q Exactive HF hybrid quadrupole-Orbitrap mass spectrometer (Thermo Scientific). Proteins from the samples were identified at the Biological Mass Spectrometry Facility at Rutgers University.

Amino Acid Composition Analysis

Transgenic mature kernels were ground to fine powder and about 10 mg were used for amino acid composition analysis conducted by the Proteomics and Mass Spectrometry Facility at the Donald Danforth Plant Science Center, St. Louis, Mo. Samples were pretreated with performic acid prior to acid hydrolysis, yielding the acid stable forms cysteic acid and Met sulfone that can be measured by separation on a UPLC column. Tryptophan was not detected following acid hydrolysis.

Chick Feeding Trials.

The research protocol (Protocol No. 16-049) for chick feeding trial was approved by Rutgers University's Institutional Animal Care and Use Committee and followed the guidelines contained in the Guide for the Care and Use of Laboratory Animals (National Research Council) and applicable provisions of the Animal Welfare Act. Day-old male broiler chicks (Cornish Cross) were housed in the brooder barn in pens provided with overhanging heaters maintained at 90° F. for the first 2 wk and reduced to 85° F. on the third week. A 14-h fluorescent illumination was provided per day, and feed and water were supplied ad libitum. The birds were acclimatized to the barn conditions until day 4. On day 5, 45 chicks within a weight range of 77-87 g were randomly assigned to nine pens of five chicks each, covering three dietary treatments of a corn-soybean meal preparation (28). Each experimental diet was fed to three replicate pens over the course of 4 wk. Group body weights and feed intake per pen were recorded at weekly and daily intervals, respectively. A notable difference was observed in the efficiency of feed use, which is the feed conversion ratio (FIG. 10), between the three experimental diets. Chicks fed the normal and reference diets consumed the same amount of feed that were converted into body weight, whereas those subsisting in PE5-B101 consumed less amount of feed for the same amount of weight gain.

Corn meals from PE5-B101 and its null segregant were obtained from ears collected from about 1,000 plants for each genotype. Ears were obtained from plants that were either selfed or backcrossed to the inbred B101 and were grown in the greenhouse.

Results

The High-Met transgenic maize PE5 event (Planta et al.) was crossed with an α-zein RNAi line (Wu and Messing 2011). Crosses of PE5 with suppression lines of β- and γ-zeins were also performed as redistribution of protein sulfur in seeds occurs when accumulation of sulfur-containing zeins are reduced (Wu et al. 2012) or when a sulfur-rich protein is synthesized in transgenic maize seeds (Molvig et al. 1997; Lai and Messing 2002; Tabe and Droux 2002; Hagan et al. 2003; Chiaiese et al. 2004).

Reduction lines of α-, β-, and γ-zeins can be achieved through RNAi (FIG. 1). Transgenes for the RNAi lines have inverted repeats of the target sequence or sequences separated by a partial GFP linker. The αRNAi construct has a tandem cassette of a 19- and 22-kDa α-zein genes and targets both α-zeins, γRNAi has an inverted repeat of the 27-kDa γ-zein gene but cross reacts with the 16-kDa γ-zein to target both 16- and 27-kDa γ-zeins, whereas βRNAi targets the 15-kDa β-zein (Wu and Messing 2010; Wu and Messing 2011).

PE5 is a high-Met transgenic maize that ectopically and leaf-specifically expresses the PepC promoter-driven *E. coli* enzyme 3'-phosphoadenosine-5'-phosphosulfate reductase, or EcPAPR (Planta et al.). EcPAPR is an enzyme involved in reductive sulfate assimilation (Martin et al. 2005). This transgenic PE5 line exhibits an increased kernel Met content when used as the maternal parent (FIG. 2A). PE5 plants were therefore crossed with the zein reduction lines as the pollen donor to manifest the increased seed Met phenotype in resulting ears.

Rebalancing of the Protein S in Different Stacked Events

Five types of distinct ears were obtained from the crosses of PE5 with the different zein reduction lines: (1) PE5;α-, (2) PE5;γ-, (3) PE5; β-, (4) PE5;γ-/α- and (5) PE5;γ-/β-. At least 14 kernels from each transgenic ear were analyzed individually by phenotyping with SDS-PAGE or genotyping for the RNAi transgenes. Kernels were then pooled depending on whether they were segregating or non-segregating for the RNAi transgenes (FIG. 2B).

Loss of β- and γ-zeins promotes a much higher increase in the accumulation of the Met-rich 10-kDa δ-zein compared to the reduction in the S-poor α-zeins (FIG. 2B). This increase in the accumulation of the 10-kDa δ-zein was previously demonstrated in transgenic maize expressing the β- and γ-zein RNAi transgenes (Wu et al. 2012), although it was not as high as when these RNAi transgenes were stacked with the PE5 event (FIG. 2B, upper panel). Reduction in both β- and γ-zeins channels even more protein sulfur to the 10-kDa δ-zein than the loss of either β- or γ-zein. We confirm here that enhanced assimilation of sulfur in the source leaf tissues increases accumulation of the S-containing zeins in the seed sink tissues, and also show that loss of the S-containing zeins reallocates the protein S to the remaining or available S-containing zeins.

PE5 Influences Kernel Opacity Depending on Zein Gene Expression

Figure 3A:
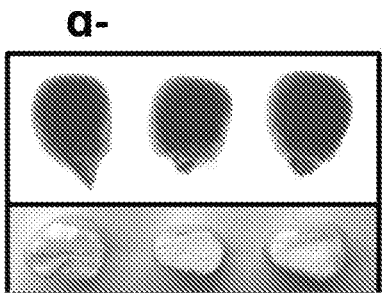
Figure 3D:
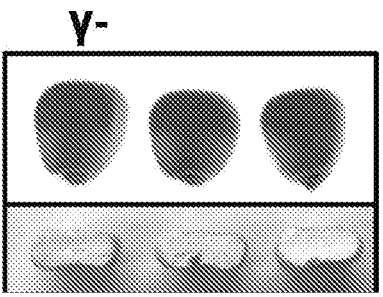
Figure 3G:
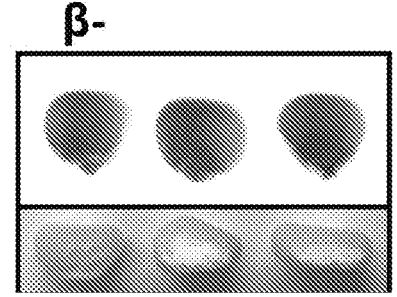
Figure 3B:
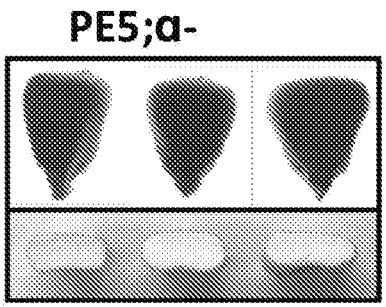
Figure 3E:
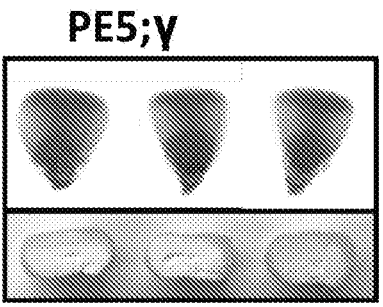
Figure 3H:
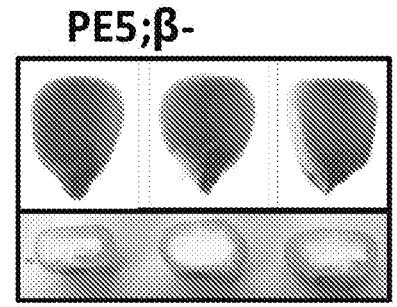
Figure 3C:
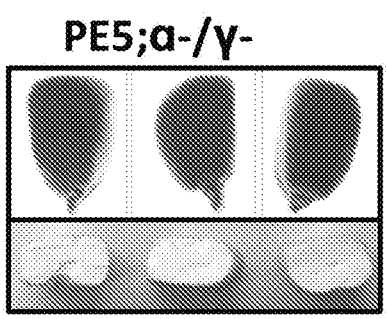
Figure 3F:
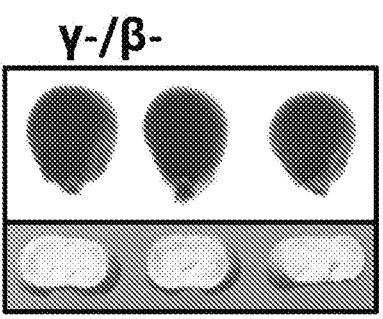
Figure 3I:
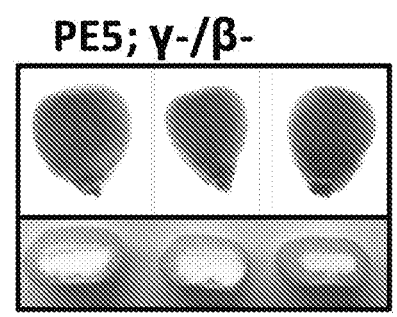

As the loss of α- and γ-zeins by RNAi induces a full or partial opaque seed phenotype, respectively (Segal et al. 2003; Wu and Messing 2010), hybrid kernels were inspected whether the PE5 transgenic event affects endosperm modification. Opacity of the hybrid PE5;zein RNAi kernels were phenotyped with a light box (FIG. 3). Loss of β-zeins did not change the phenotype of the vitreous kernel, as indicated by the thick outer layer of the vitreous endosperm in sliced kernels (FIG. 3G). Reduction in the γ-zeins produced a partial opaque phenotype, where the regular pattern of endosperm modification extends from the crown midway to the base of the kernel (FIG. 3D), whereas reduction in both β- and γ-zeins produced complete opaque kernels (FIG. 2F). However, combining PE5 with reduction in both β- and γ-zeins completely restored the vitreous kernel phenotype (FIG. 2I). This reversion to amore vitreous phenotype was also observed in PE5;γ- kernels (FIG. 2E). As βRNAi kernels are vitreous, combining it with PE5 did not change its kernel phenotype (FIG. 2H). Stacking of PE5 with αRNAi (FIG. 2B) or α/γRNAi (FIG. 2C) did not alter the opacity of the hybrid kernels. The PE5 transgenic event in PE5;γ- or PE5;γ-/β- can influence endosperm modification depending on which RNAi event is used.

Kernels from a cross of PE5 with αRNAi showed increased level of the 27-kDa γ-zein (FIG. 2B). This increase in the γ-zein was also observed in crosses of αRNAi with other transgenic events overexpressing EcPAPR (FIG. 4) and seems to be a response to the decreased levels of α-zeins. Segal et al. (2003) and Huang et al. (2004), however, reported in their zein reduction lines varying and reduced levels, respectively, of the 27-kDa γ-zein. They attributed this to segregation of the 27-kDa γ-zein gene from the A and B lines used for transformation (Segal et al. 2003) and gene silencing of the 27-kDa γ-zein gene due to the use of the γ-zein promoter in the transgenic expression cassettes (Huang et al. 2004).

QPMs have reduced levels of the 22-kDa α-zein but have two- to three-fold increase in the 27-kDa γ-zein (Ortega and Bates 1983; Wallace et al. 1990). The increase in the 27-kDa protein correlates, and is necessary, if not sufficient, for endosperm modification (Lopes and Larkins 1991; Wu and Messing 2010). Depending on the genetic background, maize inbreds can have one or two copies of the 27-kDa γ-zein gene (Das and Messing 1987; Das et al. 1991). Therefore, the effects of increased synthesis of the 27-kDa protein is that suppressors of the opaque phenotype in the seeds correspond to additional copies of the γ-zein genes. To explore this possibility, DNA was isolated from PE5 and αRNAi, their hybrid, and their parental lines to determine the nature of the γ-zein alleles (FIG. 5).

Two highly-similar tandemly-duplicated genes of the 27-kDa γ-zein, "A" and "B", in inbreds like W22 and A188, have different PstI recognition sites, which was utilized for the cleaved amplified polymorphic sequence assay (CAPS; FIG. 5A). The inbred line, A188, can have a single rearranged B gene (Rb) originating from a homologous recombination at the highly conserved 5' regions of the two repeats (Das and Messing 1987; Das et al. 1991).

The DNA gel profile in FIG. 5B shows the utility of the assay in determining allelic variations in the 27-kDa γ-zein genes from different maize inbred lines. Hi-II A×B, B101, PE5, αRNAi, and kernels from a PE5×αRNAi cross (FIG. 5B-5C) have a single copy of the γ-zein gene. There seems to be no copy number variation in the hybrids and inbreds related to PE5 and αRNAi, and thus, unlikely that modifiers of the opaque phenotype are associated with copy number variations of the γ-zein genes in our crosses. Indeed, γ-/β- is opaque (FIG. 3F), but PE5;γ-/β- is vitreous (FIG. 3I), exemplifying restoration of the normal phenotype in the absence of the γ-zeins, but in the presence of PE5. On the other hand in the absence of PE5, a duplication of the 27-kDa γ-zein gene in QPMs enhances its expression and promotes endosperm modification (Liu et al. (2016).

Protein Accumulation Patterns in PE5;Zein RNAi Kernels

To determine whether the protein accumulation patterns are different between the transgenic zein reduction and non-transgenic controls, kernels from an ear of a PE5×RNAi cross were pooled depending on the segregation of the RNAi transgenes. Total protein and the non-zein protein fractions were extracted from these kernels and separated in an SDS-PAGE gel (FIG. 6). Aside from the reduction in zeins due to the RNAi transgenes, PE5;γ- and PE5;β- kernels had similar protein accumulation profiles compared to their PE5;non-RNAi controls (FIG. 6A). On the other hand, reduction in α-zeins in kernels of PE5; α- and PE5;α-/γ- had different seed protein accumulation patterns than their corresponding PE5;non-RNAi kernels (FIG. 6A, 6B). The loss of α-zeins conditioned an increase in the accumulation of non-zein proteins in the kernel. Proteins in the range of 60-70 and 45-55 kDa were differentially upregulated in the α-zein-mutant kernels.

Two protein bands with sizes of about 60- and 65-kDa (red arrows in FIG. 6A) were particularly increased in PE5; α- and PE5;α-/γ- kernels, with the latter having more accumulation of these upregulated proteins than the former. These protein bands were identified by mass spectrophotometric analysis. Spectral quantitation showed that the upper band had 52.1% (316 out of 606) and the lower band had 29.8% (909 out of 3,048) of its identified peptides to be fragments of the globulin-1 (GLB1) protein. GLB1 has no known enzymatic function, and just like zeins, is thought to function as a storage protein (Kriz 1989). Pulse-chase labeling and in vitro translation studies showed that the primary translation product of Glb1 undergoes at least three post- and/or cotranslational processing steps to produce the mature GLB1 protein (Kriz and Shwartz 1986). The lower band of ~60 kDa would therefore represent the mature GLB1, whereas the upper band of ~65 kDa would be the processing intermediate GLB1'. GLB1 is mostly an embryo-specific protein that is estimated to account for 10-20% of the total embryo protein along with GLB2 (Kriz 1989). As the deduced amino acid composition of GLB1 has 4.11% Lys (Belanger and Kriz 1989), an increased accumulation of this Lys-rich protein could contribute to an increase in the content of protein-bound Lys in the kernel. Although the 27-kDa γ-zein was increased in PE5; α- kernels, the increase in kernel Lys could not be attributed to over-accumulation of this protein as γ-zein is devoid of Lys (Table 1).

Loss of α-zeins redistributes the nitrogen, primarily stored in asparagine and glutamine in α-zeins (Table 1), to the non-zein protein fraction by compensatory increases in proteins in this fraction. Puckett and Kriz (1991) and Hunter et al. (2002) showed that GLB1 is upregulated in o2 mutants, along with other Lys-rich proteins that contribute to an increase in the kernel Lys content. Proteins that were upregulated in o2 kernels, such as GLB1 (Puckett and Kriz 1991; Hunter et al. 2002) and the Lys-rich (>8% Lys residues) glyceraldehyde-3-phosphate dehydrogenase (Damerval and Le Guilloux 1998), were also confirmed in the transgenic α-zein reduction lines (Frizzi et al. 2010).

TABLE 1

Number of amino acid residues in mature zeins. Included are zeins that are soluble in a 70% ethanol/2% beta-mercaptoethanol solution and easily discernible in a 15% SDS-PAGE gel.

| Amino acid | Number of residues | | | | | |
|---|---|---|---|---|---|---|
| | 22-kDa α-zein | 19-kDa α-zein | 16-kDa γ-zein | 27-kDa γ-zein | 15-kDa β-zein | 10-kDa δ-zein |
| Alanine | 30-36 | 27-35 | 13 | 10 | 24 | 7 |
| Arginine | 2-3 | 1-5 | 3 | 5 | 6 | 0 |
| Asparagine | 12-13 | 10-13 | 1 | 0 | 0 | 3 |
| Aspartic acid | 0-1 | 0-1 | 0 | 0 | 5 | 1 |
| Cysteine | 1 | 1-2 | 12 | 15 | 7 | 5 |
| Glutamic acid | 1-2 | 1-2 | 3 | 2 | 3 | 0 |
| Glutamine | 41-53 | 39-47 | 31 | 30 | 21 | 15 |
| Glycine | 3-4 | 2-6 | 15 | 13 | 16 | 4 |
| Histidine | 2-7 | 1-4 | 4 | 16 | 8 | 3 |
| Isoleucine | 8-12 | 9-12 | 1 | 4 | 6 | 3 |
| Leucine | 40-44 | 38-52 | 14 | 19 | 17 | 15 |
| Lys | 0-1 | 0-1 | 0 | 0 | 0 | 0 |
| Met | 3-6 | 0-2 | 3 | 1 | 12 | 29 |
| Phenylalanine | 3-9 | 12-14 | 7 | 2 | 1 | 5 |
| Proline | 19-22 | 18-24 | 25 | 51 | 15 | 20 |
| Serine | 14-17 | 9-17 | 9 | 8 | 12 | 8 |
| Threonine | 7-9 | 5-10 | 6 | 9 | 3 | 5 |
| Tryptophan | 0-1 | 0 | 1 | 0 | 3 | 0 |
| Tyosine | 7-8 | 8-10 | 8 | 4 | 7 | 1 |
| Valine | 13-17 | 5-13 | 8 | 15 | 5 | 5 |
| Total mature residues[1] | 233-248 | 212-246 | 164 | 204 | 171 | 129 |
| Gene model/ NCBI Accession[2] | GRMZM2G397687 GRMZM2G160739 GRMZM2G044625 GRMZM2G346897 GRMZM2G044152 GRMZM2G088365 GRMZM2G088441 | GRMZM2G059620 GRMZM2G008913 GRMZM2G008341 GRM2M2G353272 GRMZM2G053120 GHM2M2G353268 GRMZM2G404459 AF546188.1_FG005 AF546188.1_FG007 AF546187.1_FG007 AF546187.1_FG001 | GRMZM2G060429 | GRMZM2G138727 | GRMZM2G086294 | AF371266 |
| Gene name/ Subfamily | z1C1_1; z1C1_5; z1C1_8; z1C1_10; Z1C1_12; z1C1_20; z1C2 | z1A1_2; z1A1_4; z1A1_5; z1A1_6; z1A1_7; z1A2_1; z1A2_2; z184; z186; z1D2; z1D4 | 16-kDa γ-zein | 27-kDa γ-zein | 15-kDa β-zein | 10-kDa δ-zein |
| % transcript abundance in the endosperm[3] | 6.0 | 24.0 | 2.9 | 5.4 | 4.7 | 0.5 |
| % total zeins[4] | 20 | 40 | <5 | 20 | 10 | <5 |

[1]Mature peptides were predicted from the full-length primary translation products by the signal peptide cleavage site prediction software SignalP (PETERSEN et al. 2011)
[2]Full-length transcripts (containing both start and stop codons and with no premature stop codon) that were detected in the developing endosperm of B73 were culled from the transcrpitome data of WOO et al. (2001) and CHEN et al. (2014).
[3](WOO et al. 2001)
[4]Percent abundance relative to total zeins (THOMPSON AND LARKINS 1994).

Amino Acid Composition Analysis of PE5;Zein RNAi Kernels

The o2 mutant has about twice the Lys content compared to normal phenotype (Mertz et al. 1964) and mutant o2 alleles in different backgrounds display variations in Lys contents and penetrance of the opaque phenotype (Balconi et al. 1998; Hunter et al. 2002). Of the crosses of PE5 with different RNAi lines, only PE5;α-, PE5;γ-, and PE5;α-/γ- kernels have statistically significant higher Lys content over the normal A×B kernels (FIG. 7A). Both PE5; α- and PE5;α-/γ- kernels have higher Lys contents, with 7.25 and 5.29 mol %, respectively, than the high-Lys mutant W64Ao2. The Lys contents in these two genotypes were 60% and 128.2% higher, respectively, compared to their corresponding PE5;non-RNAi controls (Table 2). This genotype-specific variation of the Lys contents in respect to their controls suggests that also hybrid genetic backgrounds have an impact on Lys accumulation. Compared to the A×B kernels, PE5; α- kernels had 151.9% and PE5;α/γ- kernels had 83.8% more Lys. As previously reported, our αRNAi line had only a 26.7% increase in Lys content compared to the parent non-transgenic control (Wu and Messing 2011), suggesting that the high-Met PE5 maternal background also influences Lys accumulation in the seeds. Due to the well-established correlation between the levels of tryptophan and Lys in maize protein (approximately 1 to 4), either amino acid can be used as a single parameter for evaluation of protein quality (Hernandez and Bates 1969; Villegas et al. 1984).

TABLE 2

Percent changes in the Lys and Met contents of the hybrid PE5; RNAi+ kernels relative to the PE5; RNAi− and non-transgenic A × B kernels. Data shown are means (SD) of three pooled replicates.

| | % variation from | | | | | | | | | |
|---|---|---|---|---|---|---|---|---|---|---|
| | PE5; RNAi− kernels (SD) | | | | | Non-transgenic A × B kernels (SD) | | | | |
| Amino acid | PE5; α− | PE5; γ− | PE5; β− | PE5: γ/α− | PE5: γ/β− | PE5; α− | PE5; γ− | PE5; β− | PE5; γ/α− | PE5; γ/β− |
| Lys | 60 (0.043) | 32.83 (0.129) | −20.54 (0.030) | 128.16 (0.163) | −17.26 (0.061) | 151.89 (0.236) | 63.89 (0.151) | −1.97 (0.030) | 83.80 (0.112) | 2.08 (0.076) |
| Met | −3.97 (0.018) | −4.12 (0.017) | −30.64 (0.010) | 26.38 (0.009) | 4.64 (0.030) | 0.79 (0.013) | 11.61 (0.014) | −19.35 (0.008) | 48.61 (0.006) | 22.12 (0.015) |

PE5;γ− Kernels have Significant Met and Lys Levels and are Vitreous

W64Ao2 had reduced levels of kernel Met due to reduced amounts of the 10-kDa δ- and 15-kDa β-zeins (Hunter et al. 2002). PE5;α−/γ− kernels have an increase of 26.4% more Met than its PE5;non-RNAi control (Table 2; Table 3), though it was not as high as in the parental PE5 introgressed into the B101 background (FIG. 7B). Therefore, positive regulators of expression of the 10-kDa δ-zein in the B101 background might have been lost in the hybrid kernels. Still, PE5;α−/γ− kernels have higher levels of both Met and Lys compared to the A×B and PE5;non-RNAi controls (Table 2).

Both Met and Lys can be increased by the synergistic effect of a maternal high-Met PE5 background and a combined α−/γ-zein reduction, with the hybrid genetic background of the kernel progenies affecting accumulation of these amino acids. Compared to other reports regarding increased Lys by transgenic zein reduction in maize (Table 4), our combination of PE5 with reduction in the α-zeins seems to promote the highest increase in Lys content. Although the higher Met and Lys contents of PE5;α−/γ− would make it a better animal feed alternative than the W64Ao2 kernels (FIG. 7), its opaque phenotype (FIG. 3) would preclude its general use. Therefore, the higher Met and Lys contents of the vitreous PE5;γ− would be a better alternative than the W64Ao2 kernels in terms of its nutritional quality and grain characteristics.

TABLE 3

Amino acid composition of transgenic maize kernels from a cross of the maternal PE5 plant with the zein RNAi lines (α−, γ−, β−, γ−/α−, or γ−/β-zein RNAi). Ground corn meal of bulked samples were from kernels segregating for the zein RNAi. Data shown are means (SD) of three pooled replicates. Values in bold for the RNAi kernels are statistically different from their corresponding controls (p < 0.01) of kernels that do not segregate for the RNAi transgene(s). The high-Lys opaque-2 mutant in W64A background, W64A o2, is added for comparison.

| Amino Acid[a] | mol % (SD) | | | | | |
|---|---|---|---|---|---|---|
| | W64Ao2 | PE5; α− | PE5; γ− | PE5; β− | PE5; γ−/α− | PE5; γ/β− |
| Ala | 10.06 (0.110) | 24.38 (1.000) | 29.24 (0.855) | 29.54 (1.915) | 23.99 (0.398) | 26.83 (1.692) |
| Arg | 3.70 (0.133) | 6.91 (0.745) | 5.01 (0.395) | 3.22 (0.090) | 5.05 (0.351) | 3.31 (0.751) |
| Asp | 9.83 (0.613) | 3.28 (0.439) | 2.88 (0.332) | 2.58 (0.098) | 7.63 (0.110) | 4.22 (0.949) |
| Cya | 3.21 (0.218) | 5.36 (0.438) | 3.57 (0.796) | 2.49 (0.219) | 3.58 (0.131) | 2.51 (0.330) |
| Glu | 15.09 (0.266) | 9.79 (0.870) | 10.20 (1.339) | 9.16 (0.160) | 7.40 (0.625) | 7.89 (0.792) |
| Gly | 9.28 (0.140) | 3.30 (0.384) | 2.38 (0.104) | 1.98 (0.076) | 5.22 (0.408) | 2.87 (0.704) |
| His | 2.93 (0.172) | 2.59 (0.163) | 1.35 (0.329) | 1.64 (0.042) | 2.24 (0.178) | 1.35 (0.468) |
| Ile | 3.07 (0.032) | 3.32 (0.240) | 4.36 (0.523) | 4.48 (0.454) | 3.68 (0.067) | 4.57 (0.578) |
| Leu | 7.94 (0.410) | 5.03 (0.331) | 8.30 (1.855) | 11.00 (1.695) | 7.09 (0.269) | 12.86 (1.591) |
| Lys | 4.21 (0.519) | 7.25 (0.711) | 4.72 (0.799) | 2.82 (0.185) | 5.29 (0.389) | 2.94 (0.624) |
| MetS | 2.57 (0.087) | 3.39 (0.371) | 3.72 (0.371) | 2.69 (0.301) | 4.95 (0.275) | 4.06 (0.389) |
| Phe | 2.54 (0.111) | 0.71 (0.118) | 1.05 (0.361) | 1.18 (0.272) | 1.42 (0.060) | 2.11 (0.846) |
| Pro | 9.48 (0.514) | 14.36 (0.944) | 13.95 (0.767) | 17.31 (0.551) | 12.31 (0.374) | 14.97 (0.442) |
| Ser | 5.38 (0.085) | 0.21 (0.049) | 0.13 (0.007) | 0.11 (0.006) | 0.69 (0.070) | 0.69 (0.070) |
| Thr | 3.96 (0.050) | 0.50 (0.017) | 0.44 (0.038) | 0.40 (0.015) | 1.32 (0.030) | 0.88 (0.439) |
| Tyr | 0.23 (0.025) | 0.42 (0.085) | 0.35 (0.015) | 0.34 (0.035) | 0.30 (0.036) | 0.34 (0.032) |
| Val | 6.46 (0.000) | 9.27 (0.555) | 8.38 (0.150) | 9.03 (0.139) | 7.79 (0.119) | 7.71 (1.343) |

[a] Acid hydrolysis of the sample yields the acid stable forms Cya (cysteic acid) and MetS (Met sulfone) from cysteine and Met, respectively.

TABLE 4

Reports of approaches to increasing kernel Lys content in maize by transgenic α-zein reduction.

| Transgenic approach | % increase in Lys | References |
|---|---|---|
| 22-kDa α-zein RNAi | 18.5 | (SEGAL et al. 2003) |
| 19-kDa α-zein antisense silencing | 43.9 | (HUANG et al. 2004) |
| Combination of 19-kDa α-zein RNAi and 22-kDa α-zein antisense silencing | 105.2 | (HUANG et al. 2006) |
| 19-kDa and 22-kDa α-zein RNAi | 26.7 | (WU and MESSING 2017) |

[a]Expression of a deregulated Lys biosynthetic enzyme.

TABLE 5

Percent changes in the amino acid contents of the hybrid PE5; RNAi+ kernels relative to the PE5; RNAi-segregating kernels. Data shown are means (SD) of three pooled replicates.

| Amino Acid[a] | % variation (SD) from PE5; RNAi- segregating kernels | | | | |
|---|---|---|---|---|---|
| | PE5; α− | PE5; γ− | PE5; β− | PE5; γ−/α− | PE5; γ−/β− |
| Ala | −14.81 (0.001) | 6.78 (0.002) | 7.86 (0.006) | 110.10 (0.005) | −2.02 (0.004) |
| Arg | 82.72 (0.051) | 44.06 (0.083) | −7.47 (0.030) | 126.61 (0.038) | −4.79 (0.077) |
| Asp | −24.25 (0.016) | −32.87 (0.007) | −39.86 (0.001) | 22.92 (0.008) | −1.71 (0.051) |
| Cya | 16.09 (0.011) | −8.39 (0.077) | −36.13 (0.020) | −3.33 (0.002) | −35.62 (0.024) |
| Glu | 32.06 (0.019) | 45.92 (0.051) | 31.09 (0.012) | −59.72 (0.001) | 12.92 (0.021) |
| Gly | −1.49 (0.019) | −30.41 (0.005) | −42.01 (0.003) | −23.81 (0.004) | −16.08 (0.048) |
| His | 35.30 (0.013) | −29.37 (0.037) | −13.81 (0.011) | −21.61 (0.006) | −29.2 (0.067) |
| Ile | −6.12 (0.005) | 14.24 (0.020) | 17.29 (0.015) | 22.15 (0.001) | 19.65 (0.024) |
| Leu | −37.57 (0.002) | −16.28 (0.055) | 11.03 (0.065) | −33.72 (0.001) | 29.8 (0.074) |
| Lys | 60 (0.043) | 32.83 (0.129) | −20.54 (0.030) | 128.16 (0.163) | −17.26 (0.061) |
| Phe | −40.45 (0.010) | −28.47 (0.080) | −19.13 (0.058) | −51.15 (0.001) | 44.19 (0.411) |
| MetS | −3.97 (0.018) | −4.12 (0.017) | −30.64 (0.010) | 26.38 (0.009) | 4.64 (0.020) |
| Pro | −7.33 (0.004) | −15.20 (0.003) | 5.25 (0.002) | 9.39 (0.005) | −9.00 (0.002) |
| Ser | −56.69 (0.016) | −72.22 (0.003) | −76.3 (0.002) | −87.03 (0.000) | 53.33 (0.109) |
| Thr | −47.74 (0.002) | −58.28 (0.003) | −61.46 (0.002) | −61.06 (0.000) | −16.24 (0.184) |
| Tyr | −17.65 (0.037) | −10.92 (0.018) | −14.29 (0.023) | 91.49 (0.088) | −15.13 (0.021) |
| Val | 20.7 (0.006) | 9.79 (0.002) | 18.35 (0.002) | 43.88 (0.001) | 1.05 (0.032) |

Knockdown of zeins by RNAi not only changes the accumulation profile of zeins (FIG. 2) but also the accumulation of amino acids sequestered in the reduced zeins (FIG. 8; Table 3). PE5; α− has more changes in the kernel amino acid composition compared to PE5;γ− and PE5; β− (FIG. 8A-8C). The changes in the amino acid composition of PE5;α-kernels were exacerbated by stacking it with γRNAi (FIG. 8D; Table 5). Surprisingly, the loss of the γ− and β-zeins in PE5;γ−/β− kernels (FIG. 8E; Table 5) had less variation in its amino acid composition compared to other PE5;zein RNAi kernels. The levels of seed amino acid composition in PE5;γ−/β− were like its PE5;non-RNAi control (FIG. 8; Table 5) and this might have contributed to the restoration of the vitreous phenotype in PE5;γ−/β− kernels.

PE5;γ−/β− kernels had the least similarity in terms of amino acid changes with other kernel genotypes (FIG. 8; Table 5). Of the 17 amino acids that were analyzed in PE5;α−/γ− kernels, only three amino acids were significantly not different from the PE5;non-RNAi control, whereas PE5;β−/γ− kernels only had leucine as statistically different from normal kernels. In comparison to wheat grain, maize has a high leucine content which contributes to its relatively poorer nutritional performance in human feeding trials (Kies and Fox 1972). An excess of dietary L-leucine acts as an antimetabolite of isoleucine as rats fed an excess of L-leucine in low-protein diet or diets deficient in isoleucine exhibited growth retardations (Harper et al. 1955). Only PE5;α− and PE5;α−/γ− kernels had significantly reduced leucine contents (FIG. 5; Table 5). The αRNAi lines, as well as o2, also had reduced leucine contents (Segal et al. 2003; Huang et al. 2004; Huang et al. 2006). Zeins in general, particularly α-zeins, are exceptionally rich in leucine (Table 1), and therefore, reduction in α-zeins would also decrease leucine accumulation in the kernels.

We have shown that the phenotypic plasticity of the seed storage proteins in maize can be exploited to generate maize kernels that have enhanced accumulation of the EAAs Lys and Met. To explore a sole crop animal diet of corn, transgenic zein reduction lines were crossed with the high-Met line PE5. As seed storage proteins mainly serve as the reservoir of nitrogen in the germinating maize seedling and not so much of specific amino acids, it has been proposed that seeds are functionally able to accommodate a wide range of variations in amino acid composition (Shotwell and Larkins 1991). These properties of the seed storage proteins would make a good target for improving the nutritional quality of maize either through a direct manipulation of zein synthesis (e.g., by RNAi) or by increasing the amino acid supply to the kernels due to increased source strength or through a combination of both methods.

Out of the five genotypes that were tested for enhanced accumulation of Met and Lys, only PE5;α−, PE5;γ−, and PE5;α−/γ− kernels have higher Lys and Met contents than the high-Lys W64Ao2. These kernels, however, have Met levels that are lower than that of PE5 (FIG. 7). PE5; α− and PE5;α−/γ− have opaque kernels, whereas PE5;γ− has vitreous kernels (FIG. 3).

Amino acid composition of maize kernels varies widely across different genetic backgrounds. Balconi et al. (1998) and Hunter et al. (2002) reported that the opaque mutant o1 exhibits different Lys levels in different maize genetic backgrounds. The o1 mutant has a Lys content that approximates that of the normal level, when the allele is in a W64A background (Hunter et al. 2002). However, it increased the Lys content of the inbred line A69Y as much as W64Ao2 (Balconi et al. 1998), indicating a differential response of these backgrounds to the same mutant allele. Met accumulation in PE5 also varies when this transgenic event is in different backgrounds. Introgression of PE5 to the high-Met inbred line B101 (in at least four generations of backcrosses) has higher Met content than when it is in an A×B hybrid background at the F3 generation (Planta et al.). Results reported here refer to hybrid genetic backgrounds resulting from a combination of crosses of PE5 with the transgenic zein reduction lines.

In QPMs, the RNAi-induced loss of the 27-kDa γ-zein abrogates the ability of the mo2s to restore kernel hardness, suggesting that it is necessary for endosperm modification (Wu et al. 2012). Because the 27-kDa gene does not require the O2 transcription factor for expression (Schmidt et al. 1992), it is not surprising that in absence of O2, QTLs of mo2s in QPMs can be linked to the 27-kDa γ-zein locus (Holding et al. 2008). In one example, gene duplication is implicated in the enhanced expression of the 27-kDa γ-zein for endosperm modification (Liu et al. 2016). Alternatively, enhanced mRNA transcription or stability, rather than gene amplification, was hypothesized to be the reason for enhanced expression of the γ-zein as one or two copies of the gene occurs in modified and non-modified o2 genetic backgrounds that were studied (Geetha et al. 1991). However, cleaved amplified polymorphisms exhibited no variation in 27-kDa γ-zein gene copy number of the genetic background that was used in this study (FIG. 5). Therefore, increased levels of γ-zeins in PE5; α– (FIG. 2B) and αRNAi (FIG. 9) is probably due to post-transcriptional regulation of gene expression as previously described (Geetha et al. 1991).

Whereas the increase in 27-kDa γ-zein expression in the presence of αRNAi occurred independently of the o2 mutation, it can result in kernel modification in certain genetic backgrounds (FIG. 9). It appears that kernel modification in reduced levels of α-zeins requires at least two factors: increased accumulation of the 27-kDa γ-zein and genetic modifiers of the opaque phenotype. The modifiers in Mo17 are probably dominant as it was used as the paternal parent in a cross with the maternal αRNAi line. Different genotypes studied for inheritance of modified endosperm in o2 backgrounds exhibited a complex system of genetic control involving gene dosage effects in the triploid endosperm, cytoplasm effects, and unstable and incomplete penetrance of the modifier genes. These modifier genes have either dominant, semidominant, synergistic, or recessive modes of action (Belousov 1987; Lopes and Larkins 1991).

One explanation for the increased expression of the native 27-kDa γ-zein protein could be the selection pressure on the 27-kDa γ-zein promoter used for expression of the αRNAi cassette, in a phenomenon proposed as proxy selection (Bodnar et al. 2016). In proxy selection, the increased activity of a transgene under the control of a native promoter can enhance the protein levels of the native gene with the same promoter. One complication in the use of αRNAi lines is the use of sequences or promoter of the 27-kDa gene that drive the RNAi expression cassette, resulting in variations of γ-zein levels in kernels of the progenies of these RNAi lines. In transgenic α-zein reduction lines, gene silencing could occur or accumulation of variable levels of expression of the γ-zein due to segregation of its alleles (Segal et al. 2003; Huang et al. 2004).

The increased accumulation of non-zein proteins in both the endosperm and embryo of PE5; α– and PE5;α–/γ– kernels (FIG. 6) is a response to α-zein reduction, as also evident in o2 (Hunter 2002). Because some of these non-zein proteins contain some amount of Lys residues, the effective kernel Lys is increased (Kriz 2009). Because α-zeins make up more than 30% of the total seed proteins, its loss would also entail a major reduction in the levels of N-transport amino acids like glutamine. However, o2-converted lines showed only a minor decrease in the protein content compared with the analogous normal inbred lines (Gupta et al. 1974), implying a protein N redistribution from zein to non-zein proteins. We have found that GLB1 has higher accumulation in our transgenic α-zein reduction lines, similar to what was observed in o2 (Puckett and Kriz 1991).

Reduction in γ-zeins can also induce the opaque seed phenotype, albeit at a less severe degree than the loss of α-zeins. Opacity of the β/γRNAi kernels is caused by incomplete embedding of the starch granules in the outer, vitreous endosperm rather than a reduction in the vitreous area observed in αRNAi kernels (Wu and Messing 2010). Kernels with reduced levels of γ-zein in PE5;γ– and PE5; γ–/β–, but not in PE5;α–/γ–kernels, have the vitreous phenotype (FIG. 3). This endosperm modification is probably an indirect effect of the PE5 transgenic event, where it can overcome the opaque phenotype mediated by γRNAi but not by αRNAi or α/γRNAi. Zeins confer the distinct shape to PBs and can form intra- and intercellular disulfide bonds with other proteins. α– zeins are postulated to serve as the "brick" and the γ– zeins the "mortar" in the seed during maturation and desiccation. During desiccation, the rough ER associated with the protein bodies breaks down, mixing the zeins with other components of the cytosol and associating directly with the starch granules. The peripheral 27-kDa γ-zein then serves as the "mortar" that bonds the starch granules in a proteinaceous matrix in the outer vitreous zone of the kernel, imparting the hard endosperm phenotype to the kernel (Chandrashekar and Mazhar 1999).

As a transgenic event in tobacco leaves, the 10-kDa δ-zein can form novel protein bodies, which it is unlikely the case in PE5;γ–/β–, as the δ-zein has a strong interaction with the α-zeins (Bagga et al. 1997; Kim et al. 2002). It is more likely that the 15-kDa β-zein has a redundant function with the 27-kDa γ-zein in terms of embedding the starch granules in a proteinaceous matrix because of its cysteine content. We have previously shown that PE5 increases expression of cysteine-rich non-zein proteins (Planta et al.). It is possible that one of these proteins is an accessory protein that associates with protein bodies and promotes its structural integrity.

Although QPMs have been proven to be effective, the complexity of introducing multiple, unlinked loci of mo2s into a defined o2 background has slowed the creation and widespread use of QPMs (Gibbon and Larkins 2005). Here we report a superior strategy to generate QPM with an additional high-Met content without a reduction of α-zeins, we call QPM+. PE5;γ– kernels could be generated in one generation of crossing, whereas QPMs entail generations of backcrossing the o2 mutant allele into a desirable germplasm and subsequent backcrosses of the o2-converted germplasm with the mo2s. It would take about 17 generations to convert a desirable germplasm into a QPM (Wu and Messing 2011). Even if both the γRNAi and PE5 lines are introgressed into a desirable germplasm, the eight generations it would take to make an introgression line with both the PE5 and γRNAi transgenes are still about half the time it takes to generate a classical QPM.

Chick Feeding Trials with the High-Met PE5

Ultimately, the usefulness of increased seed methionine must be judged on whether it improves nutritional value. PE5-B101 kernels were used in a 4-wk feeding trial of chicks with a corn-soybean meal formulation that is deficient in Met (28). Three diet rations, consisting of different corn meals, were tested with 5-d-old chicks: a complete diet consisting of a yellow dent corn supplemented with synthetic Met, corn meal from PE5-B101 without Met supplementation, and a reference diet composed of corn meal from null segregants derived from PE5-B101 without Met supplementation. Chicks receiving the normal diet had the biggest weight gain, although this is not significantly different from those fed with PE5- B101, whereas those fed the reference diet had the lowest weight gain (FIG. 10).

TABLE 6

| Diet | Ave. weight gain (g) | Ave. feed consumed (g) | Feed conversion ratio |
|---|---|---|---|
| Normal | 1,032.6 ± 66.4 (a) | 1,928.2 ± 49.9 (a) | 1.87 ± 0.08 (a) |
| Ref | 747.1 ± 56.2 (b) | 1,444.7 ± 83.7 (b) | 1.95 ± 0.12 (a) |
| PE5 | 911.7 ± 60.0 (a) | 1,387.4 ± 58.4 (b) | 1.53 ± 0.13 (b) |

We have shown that by enhancing sulfate assimilation in the leaf by transgenic means coupled with traditional backcross breeding into desirable genetic backgrounds, maize kernels with high Met content were produced that were of significant increased nutritional value to livestock. Increased Met sequestered in the S-rich zeins was bioavailable in the diet fed to chicks and can supplant synthetic Met supplementation needed for optimal growth. From a nutritional point of view, increasing Met rather than Cys is beneficial because, although animals are not able to synthesize Met from Cys, they are able to convert Met to Cys.

REFERENCES

Bagga, S., H. P. Adams, F. D. Rodriguez, J. D. Kemp and C. Sengupta-Gopalan, 1997 Coexpression of the Maize δ-zein and β-zein Genes Results in Stable Accumulation of δ-zein in Endoplasmic Reticulum-derived Protein Bodies Formed by β-zein. *The Plant Cell* 9: 1683-1696.

Balconi, C., N. Berardo, A. Reali and M. Motto, 1998 Variation in Protein Fractions and Nitrogen Metabolism of Developing Normal and Opaque Endosperm Mutants in Maize [*Zea mays* 810 L.]. *Maydica* (Italy).

Belanger, F. C., and A. L. Kriz, 1989 Molecular Characterization of the Major Maize Embryo Globulin Encoded by the Glb1 Gene. *Plant Physiology* 91: 636-643.

Belousov, A. A., 1987 Genetic Analysis of Modified Endosperm Texture in the Opaque-2 Maize. *Genetika* 23: 677-685.

Bodnar, A. L., M. N. Schroder and M. P. Scott, 2016 Recurrent Selection for Transgene Activity Levels in Maize Results in Proxy Selection for a Native Gene with the Same Promoter. *PLOS ONE* 11: e0148587.

Chandrashekar, A., and H. Mazhar, 1999 The Biochemical Basis and Implications of Grain Strength in Sorghum and Maize. *Journal of Cereal Science* 30: 193-207.

Chen, J., B. Zeng, M. Zhang, S. Xie, G. Wang et al., 2014 Dynamic Transcriptome Landscape of Maize Embryo and Endosperm Development. *Plant Physiology* 166: 252-264.

Chiaiese, P., N. Ohkama-Ohtsu, L. Molvig, R. Godfree, H. Dove et al., 2004 Sulphur and Nitrogen Nutrition Influence the Response of Chickpea Seeds to an Added, Transgenic Sink for Organic Sulphur. *Journal of Experimental Botany* 55: 1889-1901.

Conlon, H. E., and M. G. Salter, 2007 Plant Protein Extraction. *Methods in Molecular Biology* (Clifton, N.J.) 362: 379-383.

Damerval, C., and M. le Guilloux, 1998 Characterization of Novel Proteins Affected by the O2 mutation and Expressed During Maize Endosperm Development. *Molecular and General Genetics* 257: 354-361.

Dannenhoffer, J. M., D. E. Bostwick, E. Or and B. A. Larkins, 1995 opaque-15, a maize mutation with properties of a defective opaque-2 modifier. *Proceedings of the National Academy of Sciences* 92: 1931-1935.

Das, O. P., and J. W. Messing, 1987 Allelic Variation and Differential Expression at the 27-kilodalton Zein Locus in Maize. *Molecular and cellular biology* 7: 4490-4497.

Das, O. P., E. Poliak, K. Ward and J. Messing, 1991 A New Allele of the Duplicated 27 kD Zein Locus of Maize Generated by Homologous Recombination. *Nucleic Acids Research* 19: 3325-3330.

Frizzi, A., R. A. Caldo, J. A. Morrell, M. Wang, L. L. Lutfiyya et al., 2010 Compositional and Transcriptional Analyses of Reduced Zein Kernels Derived From the opaque-2 Mutation and RNAi Suppression. *Plant Molecular Biology* 73: 569-585.

Geetha, K. B., C. R. Lending, M. A. Lopes, J. C. Wallace and B. A. Larkins, 1991 opaque-2 Modifiers Increase γ-zein Synthesis and Alter its Spatial Distribution in Maize Endosperm. *The Plant Cell* 3: 1207-1219.

Gibbon, B. C., and B. A. Larkins, 2005 Molecular genetic approaches to developing quality, protein maize. *Trends in Genetics* 21: 227-233.

Gupta, D., I. Kovacs and L. Gaspar, 1974 Protein Quality Traits and Their Relationships With Yield and Yield Components of opaque-2 and Analogous Normal Maize Hybrids and Inbred Lines. *Theoretical and Applied Genetics* 45: 341-348.

Hagan, N. D., N. Upadhyaya, L. M. Tabe and T. J. V. Higgins, 2003 The Redistribution of Protein Sulfur in Transgenic Rice Expressing a Gene for a Foreign, Sulfur-rich Protein. *The Plant Journal* 34: 1-11.

Harper, A. E., D. A. Benton and C. A. Elvehjem, 1955 l-Leucine, an Isoleucine Antagonist in the Rat. *Archives of Biochemistry and Biophysics* 57: 1-12.

Hernandez, H. H., and L. S. Bates, 1969 A Modified Method for Rapid Tryptophan Analysis in Maize. CIMMYT, Mexico, D. F.

Holding, D. R., B. G. Hunter, T. Chung, B. C. Gibbon, C. F. Ford et al., 2008 Genetic Analysis of opaque-2 Modifier Loci in Quality Protein Maize. Theoretical and Applied Genetics 117: 157.

Huang, S., W. R. Adams, Q. Zhou, K. P. Malloy, D. A. Voyles et al., 2004 Improving Nutritional Quality of Maize Proteins by Expressing Sense and Antisense Zein Genes. *Journal of agricultural and food chemistry* 52: 1958-1964.

Huang, S., A. Frizzi, C. A. Florida, D. E. Kruger and M. H. Luethy, 2006 High Lysine and High Tryptophan Transgenic Maize Resulting From the Reduction of Both 19- and 22-1(D Alpha-zeins. *Plant molecular biology* 61: 525-535.

Hunter, B. G., M. K. Beatty, G. W. Singletary, B. R. Hamaker, B. P. Dilkes et al., 2002 Maize Opaque Endosperm Mutations Create Extensive Changes in Patterns of Gene Expression. *The Plant Cell Online* 14: 2591-2612.

Johnson, L. A., C. L. Hardy, P. Baumel, T.-H. Yu and J. L. Sell, 2001 Identifying Valuable Corn Quality Traits for Livestock Feed. *Cereal Foods World* 46(10): 472-481.

Jones, R. A., B. A. Larkins and C. Y. Tsai, 1977 Storage Protein Synthesis in Maize. <spanclass="subtitle">II. Reduced Synthesis of a Major Zein Component by the <em>Opaque</em>-2 Mutant of Maize </span>59: 525-529.

Kies, C., and H. M. Fox, 1972 Interrelationships of Leucine with Lysine, Tryptophan, and Niacin As They Influence Protein Value of Cereal Grains for Humans. *Cereal Chemistry* 49: 223-231.

Kim, C. S., B. C. Gibbon, J. W. Gillikin, B. A. Larkins, R. S. Boston et al., 2006 The maize Mucronate mutation is a deletion in the 16-kDa γ-zein gene that induces the unfolded protein response. *The Plant Journal* 48: 440-451.

Kim, C. S., Y.-m. Woo, A. M. Clore, R. J. Burnett, N. P. Carneiro et al., 2002 Zein Protein Interactions, Rather Than the Asymmetric Distribution of Zein mRNAs on Endoplasmic Reticulum Membranes, Influence Protein Body Formation in Maize Endosperm. *The Plant Cell* 14: 655-672.

Konieczny, A., and F. M. Ausubel, 1993 A Procedure For Mapping *Arabidopsis* Mutations Using Co-dominant Ecotype-specific PCR-based Markers. *The Plant Journal* 4: 403-410.

Kriz, A. L., 1989 Characterization of Embryo Globulins Encoded by the Maize Glb Genes. *Biochemical Genetics* 27: 239-251.

Kriz, A. L., 2009 Enhancement of Amino Acid Availability in Corn Grain, pp. 79-89 in *Molecular Genetic Approaches to Maize Improvement*, edited by A. L. Kriz and B. A. Larkins. Springer Berlin Heidelberg, Berlin, Heidelberg.

Kriz, A. L., and D. Schwartz, 1986 Synthesis of Globulins in Maize Embryos. *Plant Physiology* 82:1069-1075.

Krone, F. A., G. Westphal and J. D. Schwenn, 1991 Characterisation of the gene cysH and of its product phosphoadenylylsulphate reductase from *Escherichia coli*. *Molecular and General Genetics* MGG 225: 314-319.

Lai, J., and J. Messing, 2002 Increasing Maize Seed Methionine by mRNA Stability. *The Plant Journal: For Cell and Molecular Biology* 30: 395-402.

Liu, H., J. Shi, C. Sun, H. Gong, X. Fan et al., 2016 Gene duplication confers enhanced expression of 27-kDa γ-zein for endosperm modification in quality protein maize. *Proceedings of the National Academy of Sciences* 113: 4964-4969.

Lopes, M. A., and B. A. Larkins, 1991 Gamma-Zein Content is Ralated to Endosperm Modification in Quality Protein Maize. *Crop Science* 31: 1655-1662.

Martin, M. N., M. C. Tarczynski, B. Shen and T. Leustek, 2005 The Role of 5'-adenylylsulfate Reductase in Controlling Sulfate Reduction in Plants. *Photosynthesis Research* 86: 309-323.

Mertz, E. T., L. S. Bates and O. E. Nelson, 1964 Mutant Gene That Changes Protein Composition and Increases Lysine Content of Maize Endosperm. *Science* 145: 279-280.

Molvig, L., L. M. Tabe, B. o. Eggum, A. E. Moore, S. Craig et al., 1997 Enhanced methionine levels and increased nutritive value of seeds of transgenic lupins (*Lupinus angustifolius* L.) expressing a sunflower seed albumin gene. *Proceedings of the National Academy of Sciences* 94: 8393-8398.

NRC, 1988 *Quality Protein Maize*. National Academy Press, Washington, D.C.

Ortega, E. I., and L. S. Bates, 1983 Biochemical and Agronomic Studies of Two Modified Hard-Endosperm Opaque-2 Maize (*Zea mays* L.) Populations. *Cereal Chemistry* 60.

Petersen, T. N., S. Brunak, G. von Heijne and H. Nielsen, 2011 SignalP 4.0: Discriminating Signal Peptides From Transmembrane Regions. *Nat Meth* 8: 785-786.

Planta, J., X. Xiang, T. Leustek and J. Messing, in press, Engineering sulfur storage in maize seed proteins without apparent yield loss. *Proceedings of the National Academy of Sciences of the United States of America*.

Prasanna, B. M., S. K. Vasal, B. Kassahun and N. N. Singh, 2001 Quality Protein Maize. *Current Science* 81: 1308-1319.

Puckett, J. L., and A. L. Kriz, 1991 Globulin Gene Expression in Opaque-2 and Fluory-2 Mutant Maize Embryos. *Maydica* 36: 161-167.

Sattarzadeh, A., J. Fuller, S. Moguel, K. Wostrikoff, S. Sato et al., 2010 Transgenic Maize Lines with Cell Type Specific Expression of Fluorescent Proteins in Plastids. *Plant Biotechnology Journal* 8: 112-125.

Sawa, S., T. Ito and K. Okada, 1997 A Rapid Method for Detection of Single Base Changes in *Arabidopsis thaliana* Using the Polymerase Chain Reaction. *Plant Molecular Biology Reporter* 15: 179-185.

Schmidt, R. J., M. Ketudat, M. J. Aukerman and G. Hoschek, 1992 Opaque-2 is a Transcriptional Activator That Recognizes a Specific Target Site in 22-kD Zein Genes. *The Plant Cell* 4: 689-700.

Segal, G., R. Song and J. Messing, 2003 A New. Opaque Variant of Maize by a Single Dominant RNA-interference-inducing Transgene. *Genetics* 165: 387-397.

Shotwell, M. A., and B. A. Larkins, 1991 Improvement of the Protein Quality of Seeds by Genetic Engineering, pp. 33-61 in *Molecular Approaches to Crop Improvement*, edited by, E. S. Dennis and D. J. Llewellyn. Springer Vienna, Vienna.

Tabe, L. M., and. M. Droux, 2002 Limits to Sulfur Accumulation in Transgenic Lupin Seeds Expressing a Foreign Sulfur-Rich Protein. *Plant Physiology* 128: 1137-1148.

Tarczynski, M. C., M. N. Martin, B. Shen, C. Li, T. Leustek et al., 2003 Sulfate Reduction Limits Methionine and Cysteine Content in Maize Seed, in *Plant Biology*. American Society of Plant Biologists, Honolulu, Hi., USA Thompson, G. A., and B. A. Larkins, 1994 Characterization of Zein Genes and Their Regulation in Maize Endosperm, pp. 639-647 in *The Maize Handbook*, edited by M. Freeling and V. Walbot. Springer New York, N.Y., N.Y.

Tsai, C. Y., B. A. Larkins and D. V. Glover, 1978 Interaction of the opaque-2 Gene With Starch-forming Mutant Genes on the Synthesis of Zein in Maize Endosperm. *Biochemical Genetics* 16: 883-896.

Villegas, E., E. Ortega and R. Bauer, 1984 Chemical Methods Used at CIMMYT for Determining Protein Quality in Cereal Grains CIMMYT, Mexico.

Wallace, J. C., M. A. Lopes, E. Paiva and B. A. Larkins, 1990 New Methods for Extraction and Quantitation of Zeins Reveal a High Content of γ-Zein in Modified opaque-2 Maize. *Plant Physiology* 92: 191-196.

Watson, S. A., 1987 Structure and Composition, pp. 53-82 in *Corn: Chemistry and Technology*, edited by S. A. Watson and P. E. Ramstad. Am. Assoc. Cereal Chem., St. Paul, Minn.

Woo, Y.-M., D. W.-N. Hu, B. A. Larkins and R. Jung, 2001 Genomics Analysis of Genes Expressed in Maize Endosperm Identifies Novel Seed Proteins and Clarifies Patterns of Zein Gene Expression. *The Plant Cell* 13: 2297-2317.

Wu, Y., and J. Messing, 2010 RNA Interference-mediated Change in Protein Body Morphology and Seed Opacity Through Loss of Different Zein Proteins. *Plant Physiology* 153: 337-347.

Wu, Y., and J. Messing, 2011 Novel Genetic Selection System For Quantitative Trait Loci of Quality Protein Maize. *Genetics* 188: 1019-1022.

Wu, Y., W. Wang and J. Messing, 2012 Balancing of Sulfur Storage in Maize Seed. *BMC Plant Biology* 12: 77.

While certain of the preferred embodiments of the present invention have been described and specifically exemplified above, it is not intended that the invention be limited to such embodiments. It will be apparent to one skilled in the art that various changes and modifications can be made therein without departing from the scope of the present invention, as set forth in the following claims.

---

What is claimed is:

1. A method for obtaining maize with kernels that have altered essential amino acid content comprising crossing a first maize plant comprising a transgene for leaf-specific expression of 3'-phosphoadenosine-5'-phosphosulfate reductase (PAPR) enzyme with a second maize plant comprising an RNAi transgene that downmodulates expression at least one of α-zein, β-zein, or γ-zein.

2. The method of claim 1, wherein said first maize plant expressing PAPR is High-methionine.

3. The method of claim 1, wherein said PAPR enzyme is operably linked to a PepC leaf specific promoter.

4. The method of claim 1, wherein said RNAi transgene comprises at least one selectable marker or reporter gene thereby facilitating identification of progeny comprising said RNAi transgene.

5. A maize plant obtained by the method of claim 1, wherein said plant comprises a transgene for leaf-specific expression of 3'-phosphoadenosine-5'-phosphosulfate reductase (PAPR) enzyme and an RNAi transgene that downmodulates expression at least one of α-zein, β-zein, or γ-zein.

6. The maize plant method of claim 5 wherein said plant expresses an RNAi transgene targeting γ-zein and has kernels with a vitreous phenotype and increased Methionine and Lysine content.

7. The maize plant of claim 5 wherein said plant expresses RNAi transgenes targeting α-zein and γ-zein and has kernels with an opaque phenotype and increased Methionine and Lysine content.

8. The maize plant of claim 5 wherein said plant has elevated levels of GLB1 and elevated kernel Lysine content.

9. A composition comprising kernels or ground kernel material obtained from the plant of claim 5.

10. The method of claim 1 further comprising breeding a transgenic plant derived from said kernels to yield a transgenic progeny plant that comprises said PAPR transgene and said RNAi transgene, wherein kernels obtained from said progeny plant have increased levels at least one essential amino acid.

11. Seed or progeny of the plant obtained from the method of claim 10, wherein said seed or progeny comprises a transgene for leaf-specific expression of 3'-phosphoadenosine-5'-phosphosulfate reductase (PAPR) enzyme and an RNAi transgene that downmodulates expression at least one of α-zein, β-zein, or γ-zein.

12. The composition of claim 9 present in an animal feed.

13. The composition of claim 9 present in a chicken feed.

14. The method of claim 1, wherein said second maize plant expresses RNAi transgenes targeting α-zein and γ-zein or α-zein and β-zein.

* * * * *

SEQUENCE LISTING

<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
acaaccacta cctgagcac                                                    19

<210> SEQ ID NO 2
<211> LENGTH: 29
<212> TYPE: DNA
<213> ORGANISM: Artificial Sequence
<220> FEATURE:
<223> OTHER INFORMATION: primer

<400> SEQUENCE: 2
attaagcttt gcaggtcact ggattttgg                                         29

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
ctccccatcc ctatttgaac cc                                                22

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
ggtaggtttc cgggaacaag ta                                                22

<210> SEQ ID NO 5
<211> LENGTH: 19
<212> TYPE: DNA
<213> ORGANISM: Artificial Sequence
<220> FEATURE:
<223> OTHER INFORMATION: primer

<400> SEQUENCE: 5
ccacctccac gcatacaag                                                    19

```
<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
atggactgga ggaccaagc                                                19
```